United States Patent [19]

Madras et al.

[11] Patent Number: 5,506,359
[45] Date of Patent: Apr. 9, 1996

[54] COCAINE ANALOGUES AND THEIR USE AS COCAINE DRUG THERAPIES AND THERAPEUTIC AND IMAGING AGENTS FOR NEURODEGENERATIVE DISORDERS

[75] Inventors: Bertha K. Madras, Newton; Peter Meltzer, Lexington, both of Mass.

[73] Assignee: President and Fellows of Harvard College, Cambridge, Mass.

[21] Appl. No.: 111,141

[22] Filed: Aug. 24, 1993

Related U.S. Application Data

[63] Continuation-in-part of Ser. No. 934,362, Aug. 24, 1992, abandoned.

[51] Int. Cl.[6] .................................................. C07D 451/02
[52] U.S. Cl. ......................... 546/130; 546/128; 546/129
[58] Field of Search .................................... 546/129, 130, 546/128; 514/304

[56] References Cited

U.S. PATENT DOCUMENTS

| | | | |
|---|---|---|---|
| 2,799,680 | 7/1957 | Fromer | 260/294.7 |
| 3,452,029 | 6/1969 | Childress et al. | 260/292 |
| 3,813,404 | 5/1974 | Clarke et al. | 260/292 |
| 4,393,069 | 7/1983 | Langbein et al. | 424/265 |
| 5,128,118 | 7/1992 | Carroll et al. | 424/1.1 |

OTHER PUBLICATIONS

Balster et al. "Potent Substituted–3β–phenyltropane Analogs of Cocaine have Cocaine–like Discriminative Stimulus Effects" Drug and Alcohol Dependence, 29:145–151 (1991).
Boja et al. "Isothiocyanate Derivatives of Cocaine: Irreversible Inhibition of Ligand Binding at the Dopamine Transporter" Molecular Pharmacology 39:339–345 (1991).
Boja et al. "New, Potent Cocaine Analogs: Ligand Binding and Transport Studies in Rat Striatum" European J. of Pharmacology, 184:329–332 (1990).
Brownell et al. "Glucose Utilization and N–[C–11]–Methyl–2 Carbomethoxy–3–Phenyl Tropane ([C–11]PT) Studies of the Primate Model of Huntington's Disease" J. Nuclear Med. Abs., 32:981 (1991).
Canfield et al. "Autoradiographic Localization of Cocaine Binding Sites by [³H]CFT (³H]WIN 35,428) in the Monkey Brain" Synapse, 6:189–195 (1990).
Carroll et al. "Probes for the Cocaine Receptor. Potentially Irreversible Ligands for the Dopamine Transporter" J. Med. Chem., 35:1813–1817 (1992).
Carroll et al. "Cocaine Receptor: Biochemical Characterization and Structure–Activity Relationships of Cocaine Analogues at the Dopamine Transporter" J. Med. Chem., 35:969–981 (1992).
Carroll et al. "Synthesis, Ligand Binding, QSAR, and CoMFA Study of 3β–(p–Substituted phenyl)tropane–2β–carboxylic Acid Methyl Esters" J. Med. Chem., 34:2719–2725 (1991).
Carroll et al. "Synthesis and Ligand Binding of Cocaine Isomers at the Cocaine Receptor" J. Med. Chem., 34:883–886 (1991).
Chen et al. "In Vivo Binding, Internalization, and Dopamine–Releasing Effects of [H–3]–CFT (WIN 35,428): A Potential Brain Imaging Ligand for Dopamine Transporter or Cocaine . . . " Soc. Neuro. Abs., 16:309.5 (1990).
Clarke et al. "(2–exo–3–endo)–2–Aryltropane–3–carboxylic Esters, a New Class of Narcotic Antagonists" J. Med. Chem., 21:1235–1242 (1978).
Clarke et al. "Compounds Affecting the Central Nervous System. 4. 3β–Phenyltropane–2–carboxylic Esters and Analogs" J. Med. Chem., 16:1260–1267 (1973).
Cline et al. "Behavior Effects of Novel Cocaine Analogs: A Comparison with in Vivo Receptor Binding Potency" J. Pharm. & Exp. Therapeutics, 260:1174–1179 (1992).
Daum et al. "Compounds Affecting the Central Nervous System. 3.[1] 3β–Phenyltropan–2–ols" J. Med. Chem., 16:667–670 (1973).
Elmaleh et al. "N–[C–11]–Methyl–2B–Carbomethoxy–3B–Phenyl Tropane [C–11]PT) and Glucose Utilization in a Primate Model of Huntington's Disease" J. Nuclear Med. Abs., 32:552 (1991).
Elmaleh et al. "Preparation and In Vivo Imaging of N–[C–11]–Methyl–2–Carbomethoxy–3–Phenyl Tropane ([C–11]PT) in Monkey Brain" J. Nuclear Med. Abs., 32:1009 (1991).
Elmaleh et al. "PET Imaging Probes for the Cocaine Receptors: A Validation Study in a Nonhuman Primate Model" J. Nuclear Med. Abs., 33:946 (1992).
Goodman et al. "Radioiodinated 2β–Carbomethoxy–3β–(4–Chlorophenyl)–8–(3E–and 3Z–Iodopropen–2–YL)Nortropanes: Synthesis of Potential Radioligands for Mapping Cocaine Receptor . . . " J. Nuclear Med. Abs., 33:890 (1992).
Hantraye et al. "Dopamine Fiber Detection by [¹¹C]–CFT and PET in a Primate Model of Parkinsonism" Clin. Neurosci. and Neuropath., 3:265–268 (1992).
Hillier "WIN–35,428" Drugs of the Future, 5:459–460 (1980).
Horn "Dopamine Uptake: A Review of Progress in the Last Decade" Progress in Neurobiology, 34:387–400 (1990).
Innis et al. "Single Photon Emission Tomography Imaging of Monoamine Reuptake Sites in Primate Brain with [¹²³I] CIT" Eur. J. of Pharmacol., 200:369–370 (1991).
Kaufman et al. "Severe Depletion of Cocaine Recognition Sites Associated With the Dopamine Transporter in Parkinson's–Diseased Striatum" Synapse, 9:43–49 (1991).
Kitayama et al. "Dopamine Transporter Site–Directed Mutations Differentially Alter Substrate Transport and Cocaine Binding" Proc. Natl. Acad. Sci., 89:7782–7785 (1992).
Kline, Jr. et al. "Synthesis of 3–Arlecgonine Analogues as Inhibitors of Cocaine Binding and Dopamine Uptake" J. Med. Chem., 33:2024–2027 (1990).

(List continued on next page.)

*Primary Examiner*—C. Warren Ivy
*Assistant Examiner*—Evelyn Huang
*Attorney, Agent, or Firm*—Fish & Richardson

[57] ABSTRACT

Disclosed are benztropine and CFT analogs useful for imaging of cocaine receptors and treatment of cocaine abuse. Also disclosed are analogs useful for imaging and treatment of Parkinson's disease.

13 Claims, 18 Drawing Sheets

OTHER PUBLICATIONS

Leete "2–Carbomethoxy–3–tropinone: An Advanced Intermediate in the Biosynthesis of Cocaine" J. Amer. Chem. Soc., 83:6727–6728 (1983).

Madras "$^{11}$C–WIN 35,248 for Detecting Dopamine Depletion in Mild Parkinson's Disease" Annals of Neuro., 35:376–379 (1994).

Madras et al. "Stereoselective [3H]–Cocaine Binding to Membranes of Monkey Caudate–Putamen" Drug Abuse II Abs., A197, Paper No. 135.9.

Madras et al. "N–Modified Fluorophenyltropane Analogs of Cocaine With High Affinity for Cocaine Receptors" Pharmacol. Biochem. & Behav., 35:949–953 (1990).

Madras et al. "[$^3$H]CFT: A Novel High Affinity Ligand for Cocaine Receptors" Soc. for Neurosci. Abstracts, 15:803 (1989).

Madras et al. "Cocaine Receptors Labeled by [3H] 2β–Carbomethoxy–3β–(4–fluorophenyl)tropane" Molecular Pharmacology, 36:518–524 (1989).

Madras et al. "[3H]–(–)–Cocaine Binding to Membranes of Monkey Striatum" FASEB J. Abstracts, 2:A1137 (1988).

Meltzer et al. "Substituted 3–Phenyltropane Analogs of Cocaine: Synthesis, Inhibition of Binding at Cocaine Recognition Sites, and Position Emission Tomography Imaging" J. Med. Chem., 36:855–862 (1993).

Milius et al. "Synthesis and Receptor Binding of N–Substituted Tropane Derivatives. High–Affinity Ligands for the Cocaine Receptor" J. Med. Chem., 34:1728–1731 (1991).

Milius et al., "[3H]–CFT, A High–Affinity Probe for the Cocaine Receptor" Amer. Chem. Soc. Abstract, 199:1 (1990).

Neumeyer et al. "[$^{123}$I]–2β–Carbomethoxy–3β–(4–iodophenyl) tropane: High–Affinity SPECT Radiotracer of Monoaminie Reuptake Sites in Brain" J. Med. Chem., 34:3144–3146 (1991).

Patel et al. "A Cocaine Analog and a GBR Analog Label the Same Protein in Rat Striatal Membranes" Brain Res., 576:173–174 (1992).

Reith et al. "Radiolabeling of Dopamine Uptake Sites in Mouse Striatum: Comparison of Binding Sites for Cocaine, Mazindol, and GBR 12935" Arch. of Pharmacol., 345:309–318 (1992).

Ritz et al. "Cocaine Inhibition of Ligand Binding at Dopamine, Norepinephrine and Serotonin Transporters: A Structure–Activity Study" Life Sciences, 46:635–645 (1990).

Rubenstein "III Imaging With Photons" Scientific American, 1/88:1–14 (1988).

Scheffel et al. "In Vivo Labeling of Cocaine Binding Sites on Dopamine Transporters with [$^3$H] WIN 35,428" J. Pharmacol. & Exper. Therapeutics, 257:954–958 (1991).

Scheffel et al. "Cocaine Receptors: In Vivo Labeling With $^3$H–(–)Cocaine, $^3$H–WIN 35,065–2, and $^3$H–WIN 35,428" Synapse, 4:390–392 (1989).

Spealman et al. "Self–Administration of the 2β–Carbomethoxy–3β(4–Fluorophenyl)Tropane" Pharmacol. Biochem. & Behavior, 39:1011–1013 (1991).

Zakusov et al. "Pharmacology of New Tropan Derivatives" Pharm. Ther., 32:327–337 (1987).

Cutting W. C. in 'The actions and uses of drugs. Handbook of Pharmacology.' Appleton–Century–Crofts N.Y. 1969.

Van der Zee et al., "A comparison of the inhibitory effects of aromatic substituted benzhydryl . . . into synaptosomal preparations of the rat brain", *Neuropharmacology*, 17(7), 483–90, 1978.

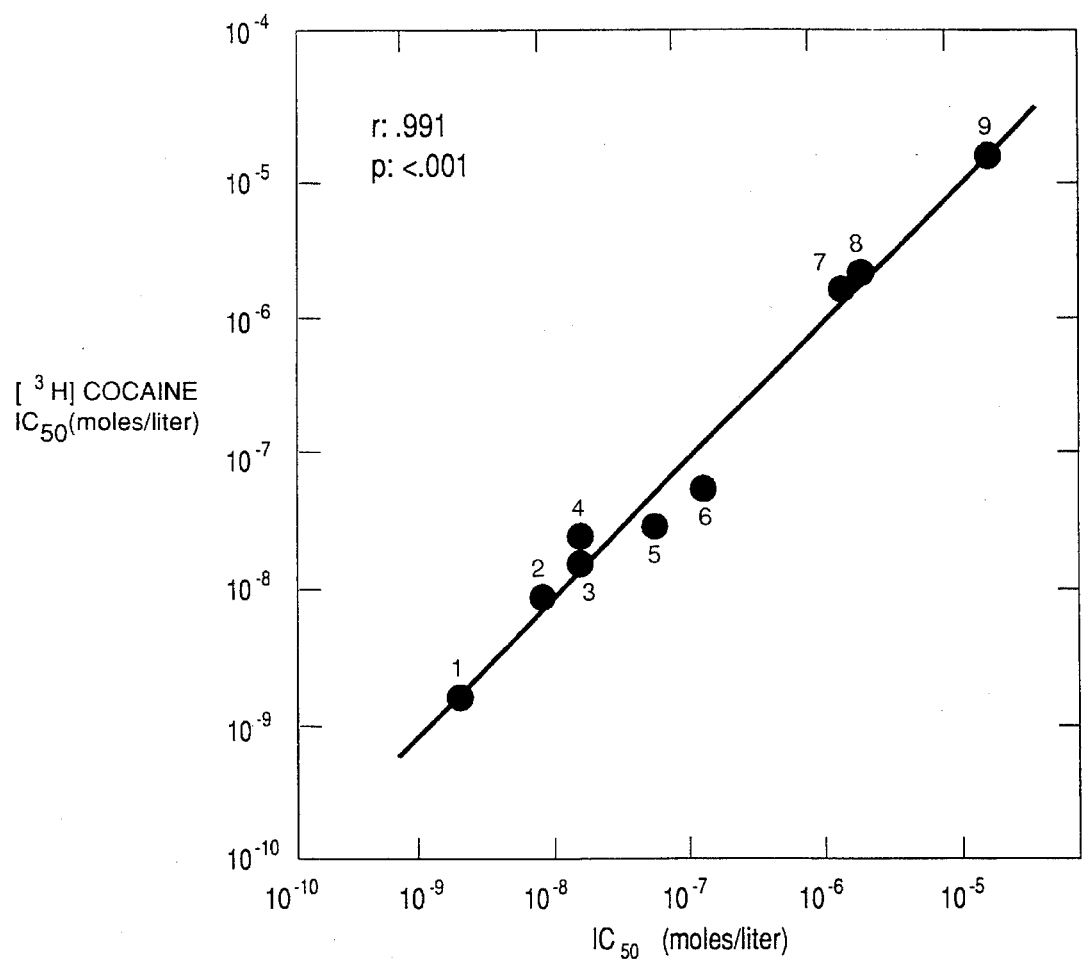
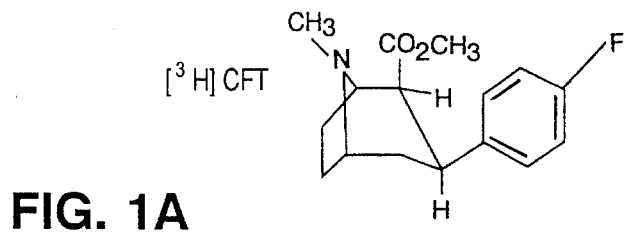
FIG. 1A

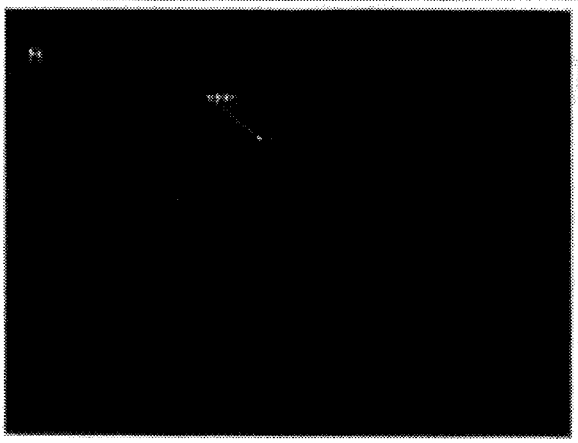
FIG. 4a-A
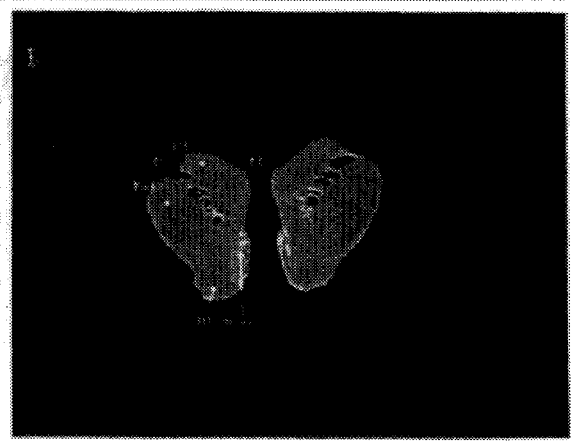
FIG. 4a-B
FIG. 4a-C
FIG. 4a-D
FIG. 4a-E
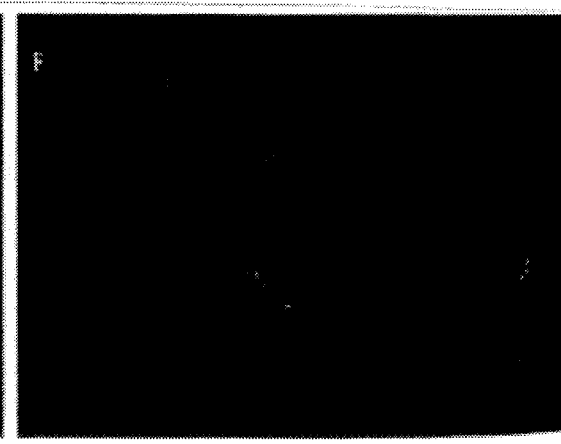
FIG. 4a-F

FIG. 4b-A   FIG. 4b-B   FIG. 4b-C   FIG. 4b-D
FIG. 4b-E   FIG. 4b-F   FIG. 4b-G   FIG. 4b-H
FIG. 4b-I   FIG. 4b-J   FIG. 4b-K   FIG. 4b-L Figure 5
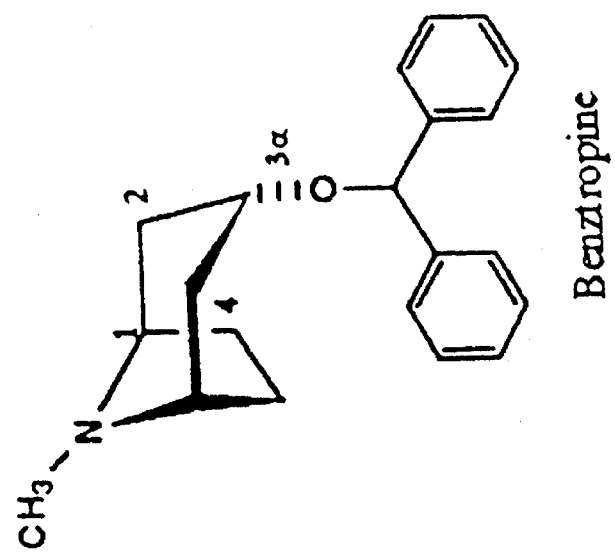
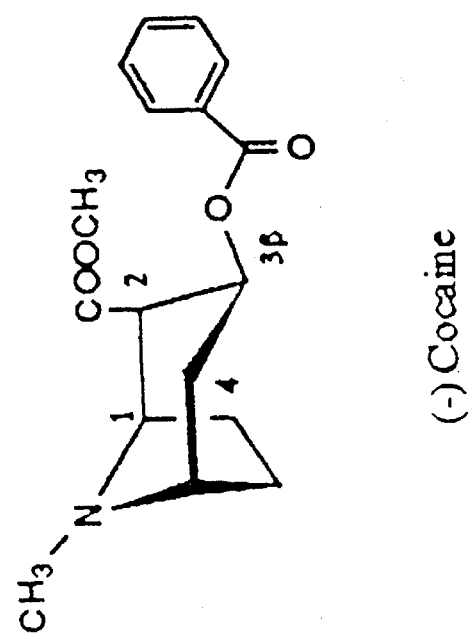
FIG. 5

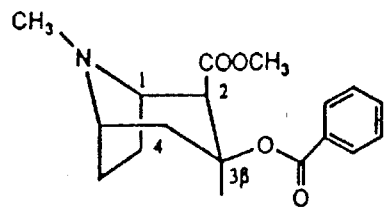
(-) Cocaine
1'
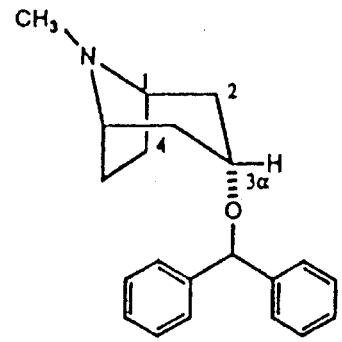
Benztropine
2'
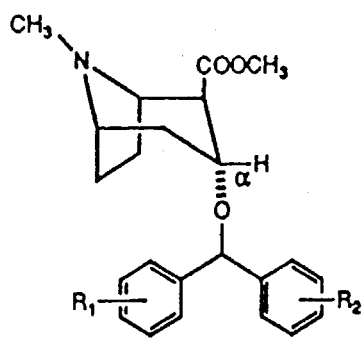
2β-carbomethoxy-3α-diphenylmethoxytropane
(2β-carbomethoxy-3α-benztropine)
3'
a. $R_1=R_2=H$
b. $R_1=R_2=4$-Cl
c. $R_1=R_2=4$-F
d. $R_1=H; R_2=4$-I
e. $R_1=H; R_2=3,4$diOX
where X=H, Acetyl, Alkyl
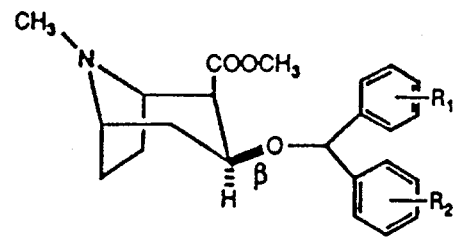
2β-carbomethoxy-3β-diphenylmethoxytropane
(2β-carbomethoxy-3β-benztropine)
4'
a. $R_1=R_2=H$
b. $R_1=R_2=4$-Cl
c. $R_1=R_2=4$-F
d. $R_1=H; R_2=4$-I
e. $R_1=H; R_2=3,4$diOX
where X=H, Acetyl, Alkyl
FIG. 5A

COCAINE ANALOGUES AND THEIR USE AS COCAINE DRUG THERAPIES AND THERAPEUTIC AND IMAGING AGENTS FOR NEURODEGENERATIVE DISORDERS

This invention was made with government support from NIDA Grant No. DA06303. The government has certain rights in the invention.

CROSS-REFERENCE TO RELATED APPLICATION

This application is a continuation-in-part of our earlier commonly owned application U.S. Ser. No. 07/934,362, filed Aug. 24, 1992, abandoned, which is hereby incorporated by reference.

BACKGROUND OF THE INVENTION

The invention relates to cocaine analogues.

The abuse of cocaine is a health problem of national significance. Despite intensive study, there is still inadequate information about the neurochemical mechanisms mediating cocaine's detrimental effects and abuse liability or about drug therapies for cocaine abuse.

Recent studies have identified biologically relevant binding sites for cocaine in brain tissue of rodents (Reith et al., Biochem. Pharmacol. 35:1123–1129, 1986; Kennedy and Hanbauer, 41:172–178, 1983; Calligaro and Eldefrawi, J. Pharmacol. Exp. Ther. 243:61–68, 1987; Calligaro and Eldefrawi, Membrane Biochem. 7:87–106, 1988), humans (Schoemaker et al., Naunyn-Schmiedeberg's Arch. Pharmacol. 329:227–235, 1985), and nonhuman primates (Madras et al., FASEB J. 2:A1137, 1988; Madras et al., ASP/ASPET Abstr. A197, 1988; Madras et al., J. Pharmacol. Exp. Ther. 251:131–141, 1989). These sites, which are associated with monoamine uptake systems, can be labeled with [$^3$H]cocaine and have properties characteristic of a pharmacological receptor. First, the sites bind [$^3$H]cocaine saturably with affinities in the $10^{-8}$ to $10^{-6}$M range, concentrations comparable to those achieved in brain or plasma after peripheral administration of cocaine to animals or humans (Van Dyke et al., Science 191.:859–861, 1976; Misra et al., Drug Alcohol Depend. Z:261–272, 1977; Javaid et al., Science 200:227–228, 1978). Second, the sites display stereoselectivity for (−)-cocaine over (+)-cocaine or its C-2 epimer pseudococaine (Madras et al., APS/ASPET Abstr. A197, 1988; Madras et al., J. Pharmacol. Exp. Ther. 251:131–141, 1989). Third, and perhaps most importantly, there is a high degree of correspondence between the relative potencies of various cocaine analogs for producing cocaine-like effects in vivo and relative binding affinities of the drugs for [$^3$H] cocaine binding sites in vitro. Specifically, the ED50 values of cocaine and several cocaine analogs for producing behavioral stimulation (Spealman et al., J. Pharmacol. Exp. Ther. 251:142–149, 1989) or for maintaining self-administration in non-human primates (Bergman et al., J. Pharmacol. Exp. Ther. 251:150–155, 1989) parallel their $IC_{50}$ values for displacing [$^3$H]cocaine from binding sites in monkey brain (Madras et al., FASEB J. Z:A1137, 1988; Madras et al., J. Pharmacol. Exp. Ther. 251:131–141, 1989).

Although cocaine inhibits the uptake of dopamine, serotonin, and norepinephrine with similar potencies, [$^3$H]cocaine recognition sites on the dopamine transporter are particularly relevant to the behavioral effects of cocaine (Reith et al., Biochem. Pharmacol. 35:1123–1129, 1986; Madras et al., FASEB J. Z:A1137, 1988; Madras et al., J. Pharmacol. Exp. Ther. 251:131–141, 1989, Bergman et al., J. Pharmacol. Exp. Ther. 251:150–155, 1989; Spealman et al., J. Pharmacol. Exp. Ther. 251:142–149, 1989). Cocaine congeners and other drugs block behaviorally relevant [$^3$H] cocaine binding in monkey caudate-putamen with a rank order of potency that corresponds closely to their reported potencies for inhibiting uptake of dopamine but not norepinephrine or serotonin (Madras et al., J. Pharmacol. Exp. Ther. 251:131–141, 1989). Furthermore, selective norepinephrine or serotonin inhibitors do not produce the characteristic stimulant, reinforcing and interoceptive effects elicited by cocaine (Spealman et al., J. Pharmacol. Exp. Ther. 251:142–149, 1989; Spealman et al., J. Pharmacol. Exp. Ther. 258:945–953, 1991; Bergman et al., J. Pharmacol. Exp. Ther. 251:150–155, 1989). Together, these studies support the view that cocaine recognition sites associated with the dopamine transporter are important mediators of the behavioral effects of cocaine.

Further clarification of the mechanisms by which cocaine and related drugs alter behavior and maintain abuse will likely emerge from molecular characterization of cocaine receptor sites and imaging these sites in the brain. These studies have been hampered, however, by the relative inefficiency of [$^3$H]cocaine as a radioligand and the lack of versatile probes to elucidate the molecular properties of the receptor complex. In particular, [$^3$H]cocaine binds to the receptor with modest affinity in all brain regions studied ($K_{0.50} \approx 300$ nM) and dissociates rapidly. This modest affinity of [$^3$H]cocaine (25–30 Ci/mmole) make it a relatively poor tag for imaging cocaine receptors, either in vitro or in vivo.

Drug therapies for cocaine abuse also are needed, and therapeutic agents based on cocaine congeners are proposed.

There is also a need for suitable agents and procedures to diagnose neurodegenerative disorders, such as Parkinson's disease. In particular, exclusion of Parkinson's disease as the cause of symptoms at an early stage may be useful information in diagnosing other conditions such as Alzheimer's disease. In addition, early diagnosis of Parkinson's disease facilitates the introduction of prophylactic drug therapy (e.g., deprenyl administration) prior to the onset of symptoms. There is also a need for compounds to neurodegenerative disorders characterized by Parkinson's disease.

SUMMARY OF THE INVENTION

Cocaine recognition sites are localized on the dopamine transporter, which itself is localized on dopamine nerve terminals. Drugs that bind to these sites therefore have potential uses which include (i) imaging probes for dopamine transporter/cocaine binding sites, (ii) imaging probes for neurodegenerative disorders, (iii) drug therapies for cocaine abuse, and (iv) drug therapies for neurodegenerative disorders such as Parkinson's disease.

Because of the unique anatomical location of the cocaine recognition sites, a high affinity probe for imaging of these sites in vivo in the brain may be carried out using, e.g., PET or SPECT imaging. Such imaging is useful for the purposes of (i) assaying cocaine receptors in chronic cocaine users and in individuals exposed to cocaine prenatally, (ii) assaying the receptor occupancy of potential cocaine therapeutics, and (iii) assaying cocaine receptors in individuals that abuse other drugs. Such imaging is also useful for monitoring the occupancy of the dopamine transporter by established and novel drugs that are targeted to and/or bind to these sites; these drugs include, but are not limited to, antidepressants (e.g., bupropion), attention deficit disorder/hyperactivity syndrome therapies (e.g., methylphenidate or pemoline), and dopamine uptake inhibitors useful for treating Parkinson's disease (e.g., benztropine, also termed cogentin). Finally, such imaging agents are useful for diagnosing or monitoring Parkinson's disease, a neurological disorder characterized by the degeneration of dopamine nerve terminals.

Apart from the uses described above, cocaine analogs may also provide alternatives to cocaine in the pharmacological management of cocaine abuse. The development of cocaine drug therapies which can be readily administered on an out-patient basis under controlled conditions may diminish the illicit drug trade, reduce the probability of AIDS transmission by frequent intravenous dose administration of cocaine, and enable abusers greater access to treatment programs.

Accordingly, one aspect of the invention features a compound of formula:

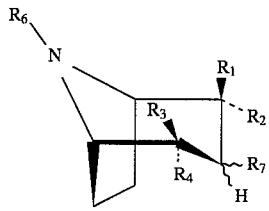

wherein the following conditions are imposed on that formula:

A. $R_1$ and $R_3$ are α-linked; $R_2$ and $R_4$ are β-linked; and $R_7$ is either α-linked or β-linked, it being understood that the —H at position 3 has a linkage opposite to $R_7$;

B. at least two of the entities $R_1$, $R_2$, $R_3$, and $R_4$ are —H,

C. at least one of the entities $R_1$, $R_2$, $R_3$, and $R_4$ is —CO—$R_5$, where $R_5$ is —$CH_3$, —$CH_2CH_3$, —$(CH_2)_nCH_3$, —$(CH_2)_n$—Z, —Z, —O—$CH_3$, —O—$CH_2CH_3$, —O—Z, —O—$CH(CH_3)_2$, —CH=$CH_2$;

where Z is $C_6H_4XY$, and X and Y are independently selected from the group consisting of: —H, —Br, —Cl, —I, —F, —OH, —$OCH_3$, —$CF_3$, —$NO_2$, —$NH_2$, —CN, —NH—CO—$CH_3$, —$N(CH_3)_2$, —$(CH_2)_nCH_3$, —CO—$CH_3$, and —$C(CH_3)_3$; and n=0–6;

D. $R_6$ is H, $CH_3$, $CH_3CH_2$, $CH_3(CH_2)_n$, $CH_2CHCH_2$, $CH_2c(C_4H_7)$, $CH_2c(C_3H_5)$, $CH_2CF_3$, $CH(CH_3)_2$, $CH_2CH_2OH$, $CH_2(CH)_nOZ'$, 2-(1-piperidinyl)ethyl, 2-(4-morpholinyl)ethyl, $(CH_2)_nC_6H_5$, $(CH_2)_nC_6H_4X$, $CH_2COCH_3$, or $XCH=CHCH_2$—, where n and X are as defined above, and Z' is —H or a straight chain alkyl group of between 1 and 4 carbons;

E. $R_7$ is

1.

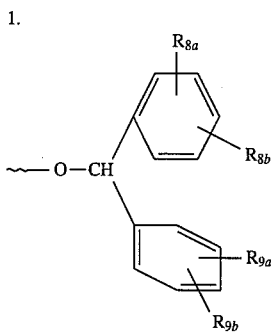

or

2.

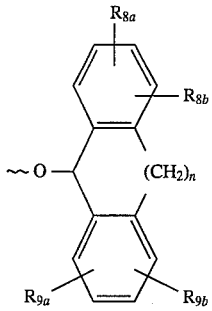

or

3.

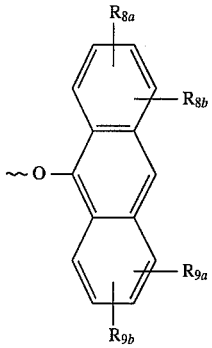

where $R_{8a}$, $R_{8b}$, $R_{9a}$, and $R_{9b}$ are independently selected from the group consisting of: —H, —Br, —F, —Cl, —I, —OH, —$COCH_3$, —$OCH_3$.

In preferred embodiments of the first apsect of the invention: a) $R_3$ is —CO—R5; b) $R_1$, $R_2$, and $R_4$ are —H; c) $R_7$ is α-linked; d) $R_6$ is —$CH_3$ or I—CH=CH—$CH_2$—; e) $R_{8b}$ and $R_{9b}$ are each —H, and $R_{8a}$ and $R_{9a}$ are substituents at the 4 position, e.g., 4-F, 4-Cl, or 4-OH (alternatively, $R_{8b}$ and $R_{9b}$ are not —H and are at the 3 position); also, the pair $R_{8a}$ and $R_{8b}$ and the pair $R_{9a}$ and $R_{9b}$, can each independently be selected from the following pairs: —H and 2-, 3-, or 4-F; —H and 2-, 3-, or 4-Cl; —H and 2-, 3-, or 4-I; 3,4-diCl; —H and 4-I; -H and-H; 3,4-diOH, 3,4-diOAc, 3,4-di$OCH_3$; 3 —OH and 4-Cl or 4-F; and 3-Cl or 3-F and 4 —OH; preferably, $R_{8a}/R_{8b}$ is —H/—H and $R_{9a}/R_{9b}$ is —H/4-F, —H/4-Cl, —H/4-I, or 3,4-diCl.

In a second aspect, the invention features, a compound of formula:

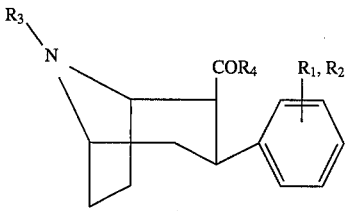

wherein $R_1$ and $R_2$ are each chosen independently from —OH, —Br, —Cl, —F, —I, —$OCH_3$, —$CF_3$, —$NO_2$, —$NH_2$, —CN, —NCS, or —OAc; or $R_1$ is —N3 and $R_2$ are each chosen from —OH, —Br, —Cl, —F, —$OCH_3$, —$CF_3$, —$NO_2$, —$NH_2$, —CN, —NCS, or —OAc; or R₁ is —H and R₂ is a substituent at position 4 chosen from: —CN, —NCS, or —OAc;

R₁ is —H and R₂ is a substituent at position 2 or 3 chosen from: —OH, —Br, —CF₃, —NO₂, —NH₂, —CN, —NCS, —OAc, —N3, —I, —Cl, —F; and wherein R₃ is —H, —CH₃, —CH₂CH₃, —(CH₂)ₙCH₃, —CH₂CH=CH₂, —CH₂c(C₄H₇), —CH₂c(C₃H₅), —CH₂CF₃, —CH(CH₃)₂, —CH₂CH₂OH, —CH₂(CH)ₙOZ, 2-(1-piperidinyl)ethyl, 2-(4-morpholinyl)ethyl, —(CH₂)ₙC₆H₅, —(CH₂)ₙC₆H₄X, or —CH₂COCH₃, wherein X is —Br, —Cl, —I, —F, —OH, —OCH₃, —CF₃, —NO₂ —NH₂, —CN, —NHCOCH₃, —N(CH₃)₂, —(CH₂)ₙCH₃, CHOCH₃, or —C(CH₃)₃; c indicates the parentheical moiety is cyclic; and n is between 0 and 6 inclusive; and wherein Z is H or a straight chain alkyl group of between 1 and 4 carbons inclusive; and wherein R₄ is —CH₃, —CH₂CH₃, —CH(CH₃)₂, —(CH₂)ₙCH₃, —(CH₂)ₙC₆H₄X, —(CH₂)ₙC₆H₄X, —C₆H₄X, —C₆H₅, —OCH₃, —OCH₃CH₂, —OCH(CH₃)₂, —OC₆H₅, —OC₆H₄X, —O(CH₂)ₙC₆H₄X, or —O(CH₂)ₙCH₃, wherein n is between 0 and 6 inclusive.

In preferred embodiments of the second aspect of the invention: R₁ and R₂ are each selected from —Cl, —OH, and —Ac; R₁ and R₂ are substituents in the 3 and 4 positions, respectively; R₁ and R₂ are both —Cl or R₁ and R₂ are both —OH; R₄ is —OCH₃; and R₁–R₃ are defined as follows:

A. R₁ is —OH, —OCH₃, —Cl, —F, or —I; R₂ is —Cl; and R₃ is —CH₃; or

B. R₁ is —Cl; R₂ is —NH₂ or —H; and R₃ is —CH₃; or

C. R₁ is —I; R₂ is —NH₂; and R₃ is —CH₃; or

D. R₁ is —N₃, —NH₂, —NCS, —OH, —OCH₃, —Cl, or —F; R₂ is F; and R₃ is CH₃; or

E. R₁ is —H, —OH, —OAc, —OCH₃, —Cl, or —F; R₂ is —OH or —OAc; and R₃ is —CH₃; or F. R₁ is —OH, —Cl, or —F; R₂ is —OH, —OCH₃, —F, —I, or —Cl; and R₃ is —CH₃; or G. R₁ is —H or —Cl; R₂ is —N₃, —NCS, or —Cl; and R₃ is —H or —CH₃.

In a third aspect, the invention features a compound of formula:

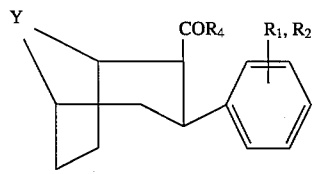

wherein Y is C, O, S, SO; or SO₂; and wherein R₁ and R₂ are each chosen independently from OH, Br, Cl, F, I, OCH₃, CF₃, NO₂, NH₂, CN, NCS, OAc, H, or N₃; and wherein R₄ is CH₃, CH₃CH₂, (CH)₂CH, CH₃(CH₂)ₙ, (CH₂)ₙC₆H₄X, C₆H₄X, C₆H₅, OCH₃, OCH(CH₃)₂, OC₆H₅, OC₆H₄X, O(CH₂)ₙC₆H₄X, O(CH₂)ₙCH₃, or OCH₃CH₂, wherein X is Br, Cl, I, F, OH, OCH₃, CF₃, NO₂, NH₂, CN, NHCOCH₃, N(CH₃)₂, (CH₂)ₙCH₃, COCH₃, or C(CH₃)3, wherein n is between 0 and 6 inclusive.

Preferably, R₄ is OCH₃; Y is C, O or S; and R₁ is H and R₂ is F, I, or Cl; or R₁ and R₂ are both Cl or OH.

In a fourth aspect, the invention features a compound of formula:

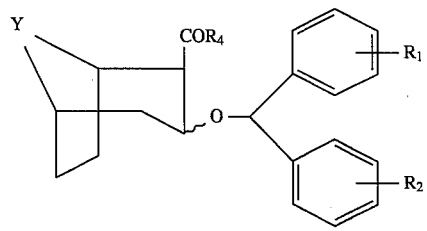

wherein Y is C, O, S, SO, or SO₂; and wherein the linkage at the 3-position is α or β; and wherein R₁ and R₂ are both 4-F, 4-Cl, 3,4-diCl, 4-I, H, 3,4-diOH, 3,4-diOAc, or 3,4-diOCH₃; or R₁ is H and R₂ is 4-F, 4-Cl, 4-I, 2-F, 2-Cl, 2-I, 3-F, 3 -Cl, 3-I, 3,4-diCl, 3,4-diOH, 3,4-diOAc, or 3,4-diOCH₃; or R₁ is H and R₂ is 3—OH—4—Cl, 3—OH—4—F, 3—Cl—4—OH, or 3—F—4—OH; or R₁ is the same as R₂ and both are chosen from 3—OH—4—Cl, 3—OH—4—F, 3—Cl—4—OH, or 3—F—4—OH; or R₁ is not the same as R₂ and both are chosen from 3—OH—4—Cl, 3—OH—4—F, 3—Cl—4—OH, or 3—F—4—OH; and wherein R₄ is CH₃, CH₃CH₂, (CH₃)₂CH, CH₃(CH₂)ₙ, (CH₂)ₙC₆H₄X, C₆H₄X, C₆H₅, OCH₃, OCH₃CH₂, OCH(CH₃)₂, OC₆H₅, OC₆H₄X, O(CH₂)ₙC₆H₄X, or O(CH₂)ₙCH₃, wherein X is Br, Cl, I, F, OH, OCH₃, CF₃, NO₂, NH₂, CN, NHCOCH₃, N(CH₃)₂, (CH₂)ₙCH₃, COCH₃ or C(CH₃)₃, where in n is between 0 and 6 inclusive.

Preferably, R₄ is OCH₃; and Y is C; and R₁ and R₂ are both F or both I; or

Y is O; the linkage at the 3-position is α; and each R₁ and R₂, independently, is Cl, I, or F.

In a preferred embodiment of all of the above aspects, the compound is labelled with a radioactive or fluorescent label; preferable labels include $^3$H, $^{11}$C (e.g., on the N-linked substituent, or less preferably, on the aromatic ring substituents) $^{123}$I or $^{125}$I or $^{18}$F (e.g., on the aromatic ring(s) of the C-3 substituent, and $^{99}$Tc (e.g., on the aromatic ring(s) of the C-3 substituent).

In a related aspect, the compounds of the invention may be formulated as therapeutic compositions, essentially including the compound in a pharmaceutically acceptable carrier.

In a fifth aspect, the invention features a method of treating cocaine addiction in a mammal, involving administering a therapeutic composition of the invention to the mammal.

In a sixth aspect, the invention features a method of selectively imaging cocaine binding regions of the central nervous system of a human patient, involving administering to the central nervous system a detectably labelled compound of the invention or CFT and detecting the binding of that compound to CNS tissue (e.g., by position emission tomography (PET) or single-photon emission computed tomography (SPECT)).

In a seventh aspect, the invention features a method of detecting parkinsonism in a human patient, involving administration to the patient of a detectably labelled compound of the invention or CFT.

In an eighth aspect, the invention features a method of treating a neurodegenerative disorder (e.g., Parkinson's disease) characterized by monoamine nerve terminal degeneration in a human patient involving administration to the patient of a therapeutic compound of the invention.

DETAILED DESCRIPTION OF THE DRAWINGS

The file of this patent contains at least one photograph executed in color. Copies of this patent with color photographs will be provided by the Patent and Trademark Office upon request and payment of the necessary fee.

FIGS. 1A and 1B are graphs showing the relationship between drug potencies at [$^3$H]CFT binding sites and drug potencies (FIG. 1A) at [$^3$H]cocaine binding sites; (FIG1B) at the dopamine transporter in the caudate-putamen.

FIGS. 4aA–4AF and FIGS. 4bA–4bL show the distribution of [$^3$H]CFT binding sites in tissue sections. FIGS. 4aA–4aF are sections in vitro and FIGS. 4bA–4bL are sections ex vivo.

FIG. 5 shows the structure of (−)cocaine and benztropine.

FIG. 5A shows cocaine and benztropine, and various analogs of those compounds.

Figure 6:
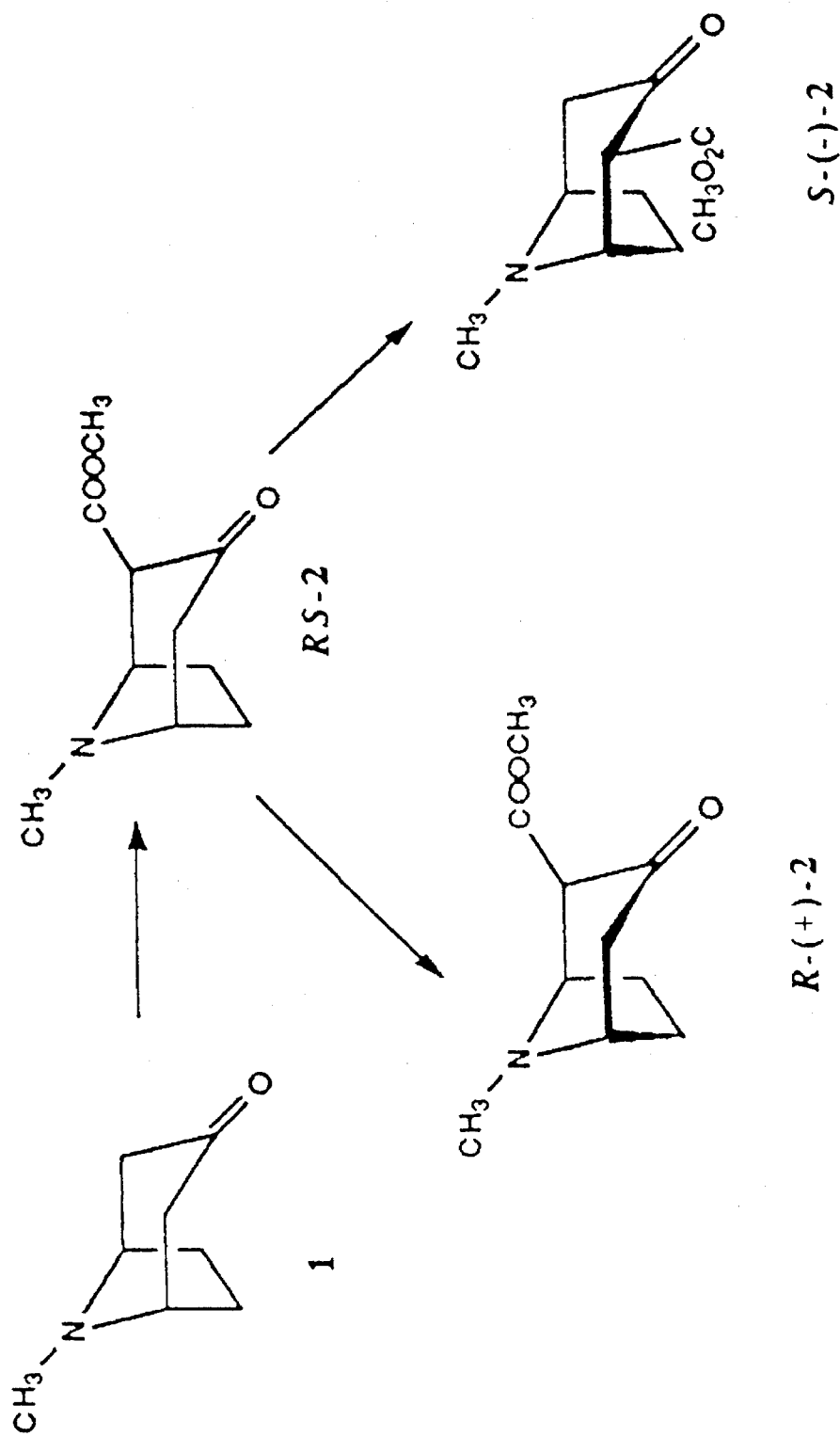
Figure 7:
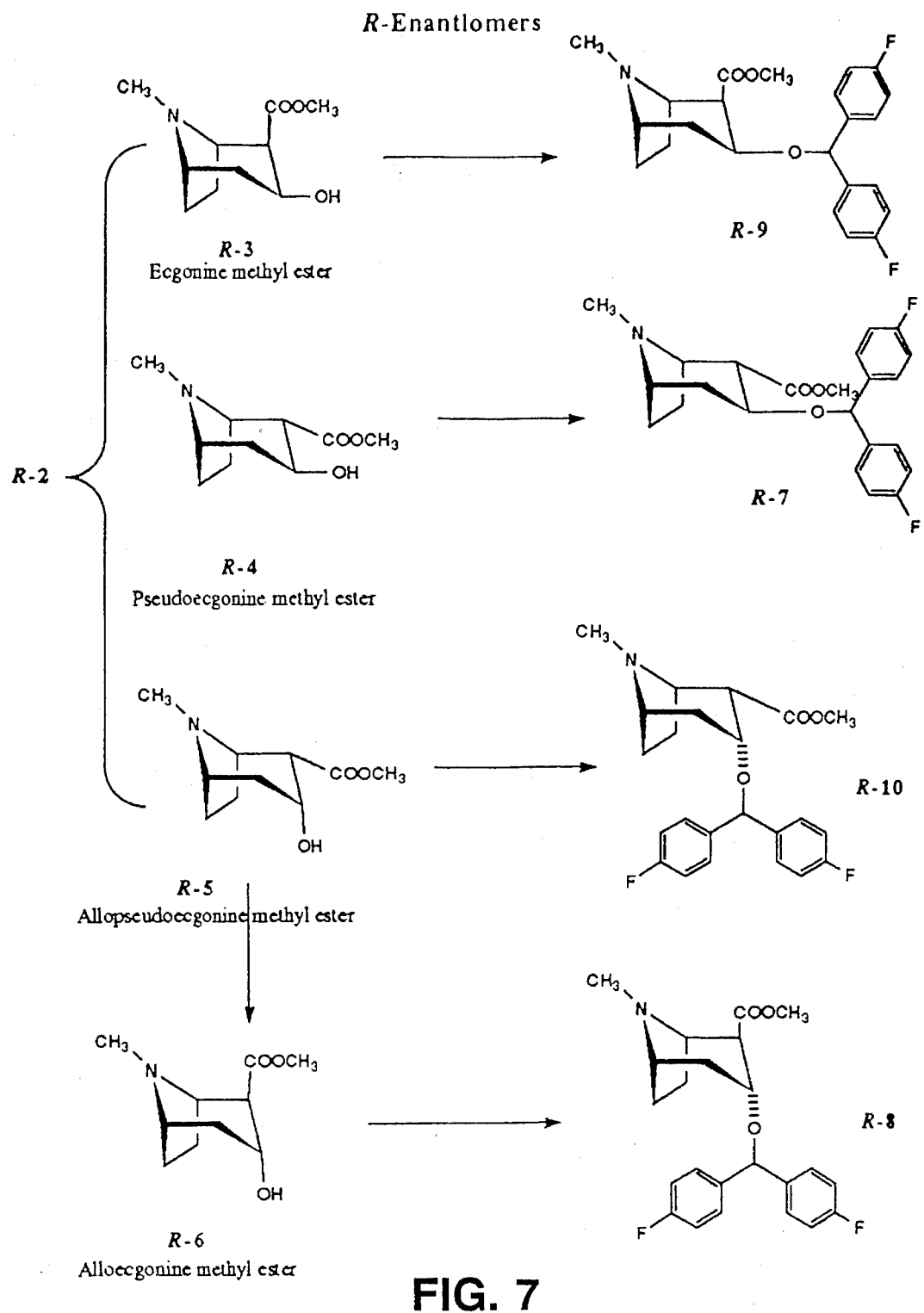
Figure 8:
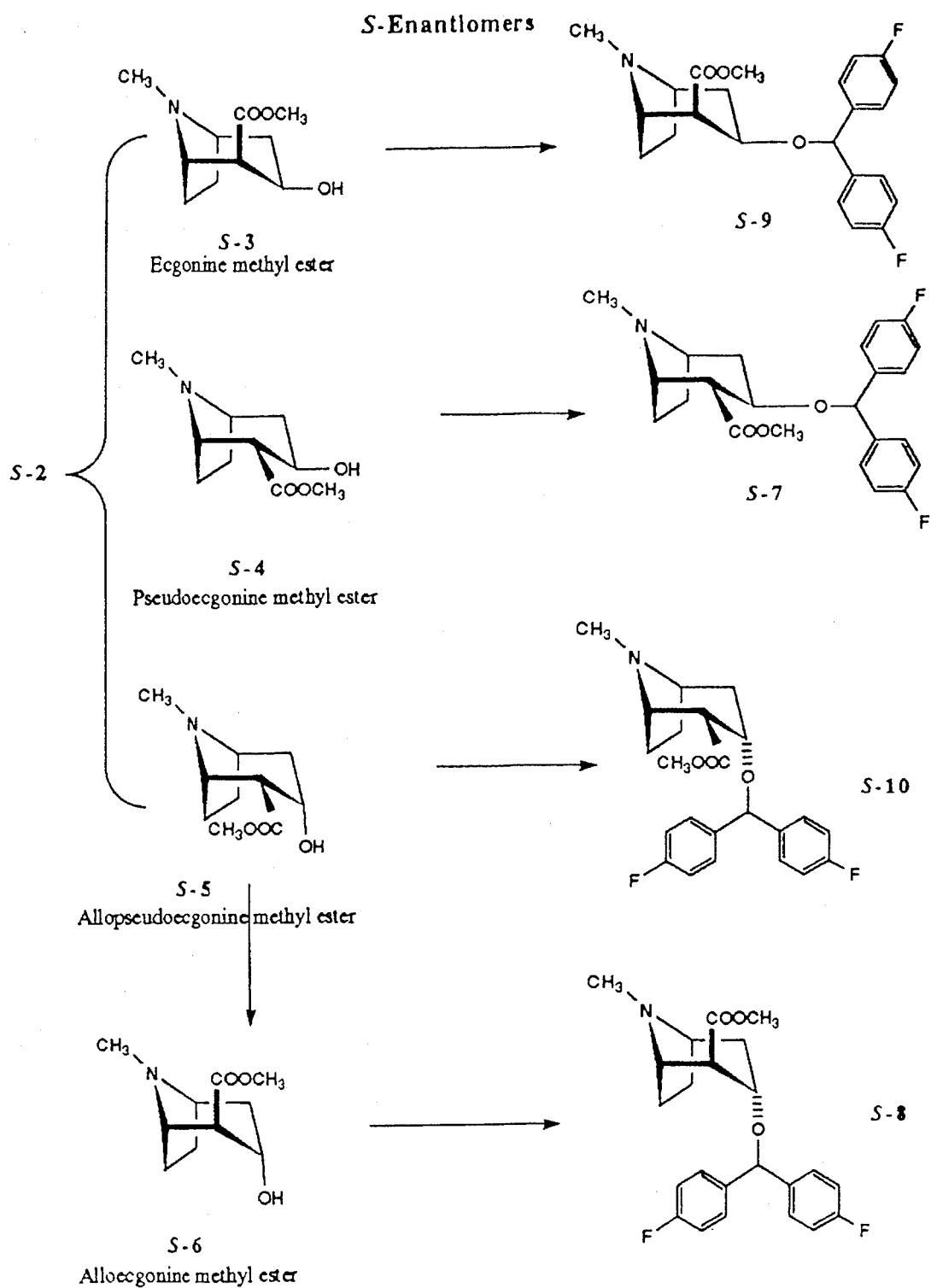

FIGS. 6–8 show synthetic schemes for preparation of various benztropane enantiomers.

Figure 9:
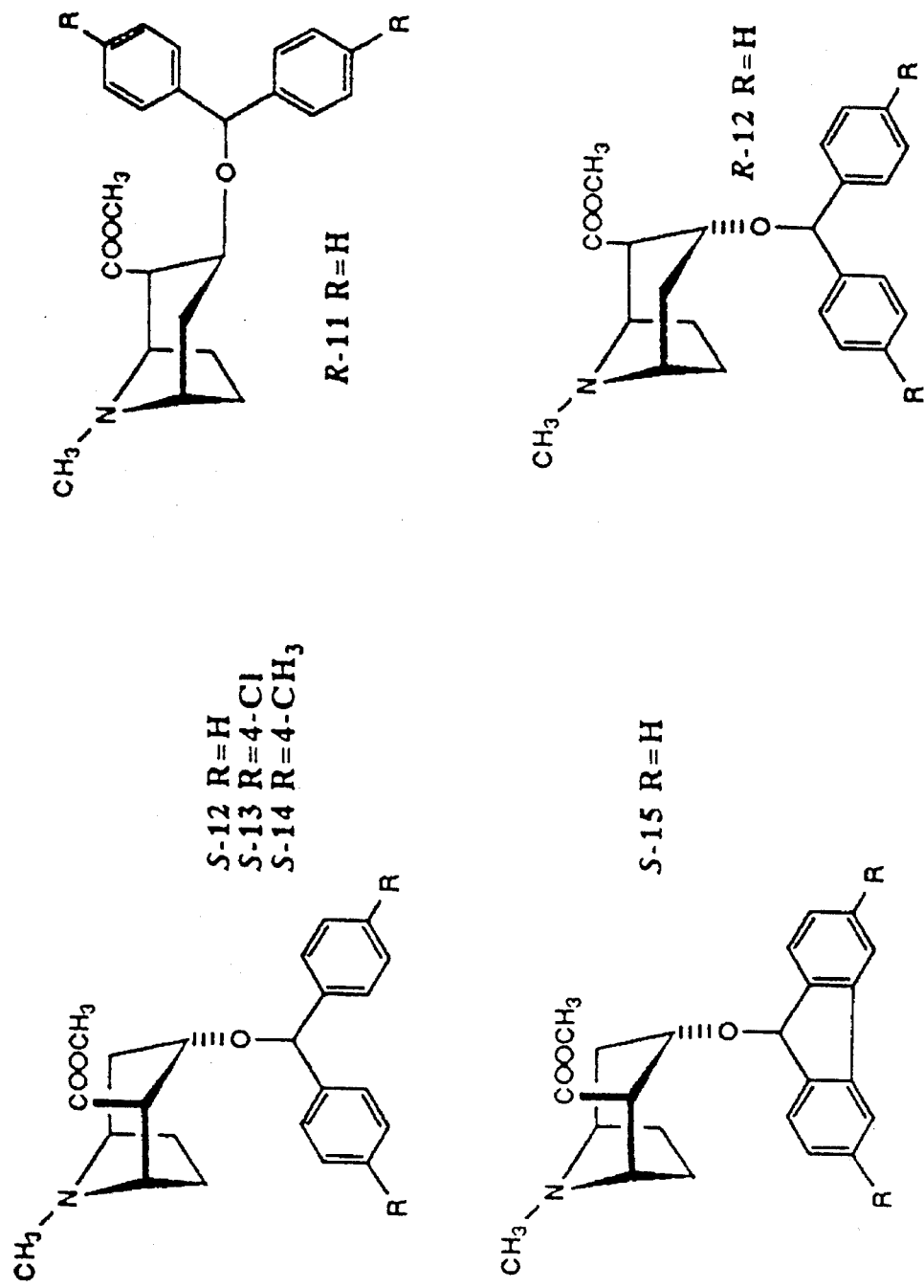

FIG. 9 shows certain alternative compounds.

Figure 10:
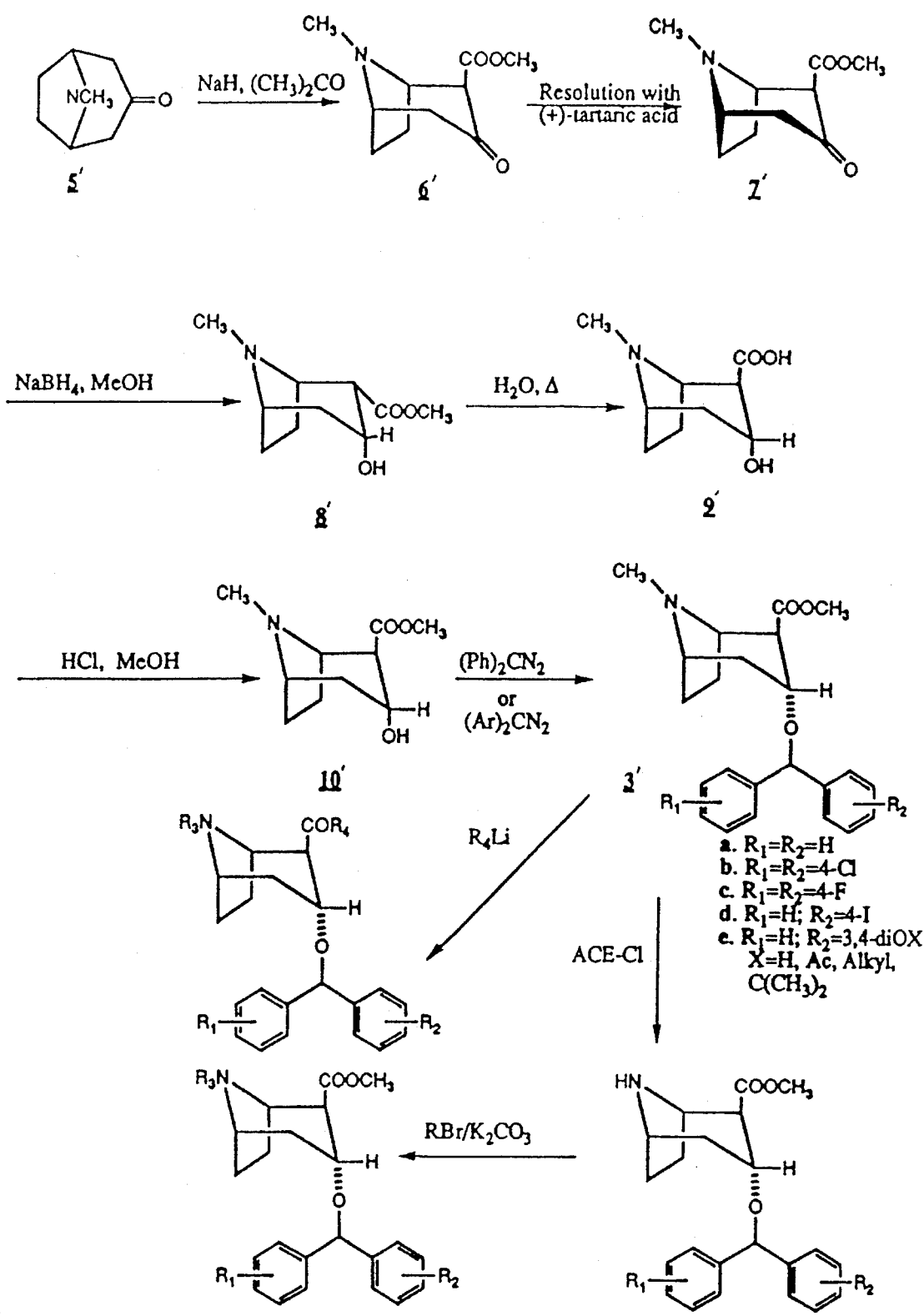

FIG. 10 shows a synthetic scheme for the preparation of 2β-carbomethoxy-3α-diphenylmethoxytropanes.

Figure 11:
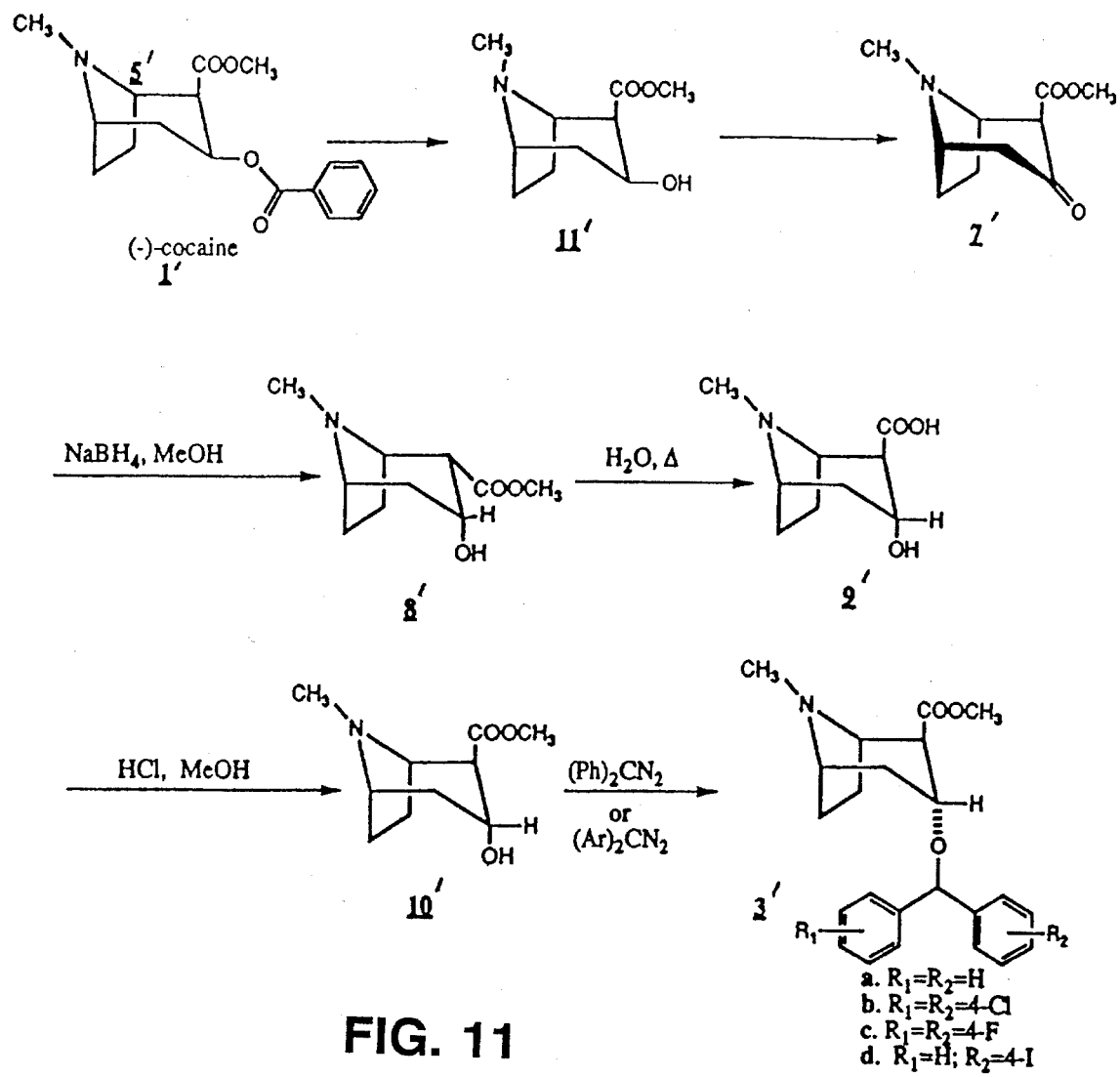

FIG. 11 shows a synthetic scheme for the preparation of 2β-carbomethoxy-3α-diphenylmethoxytropanes.

Figure 12:
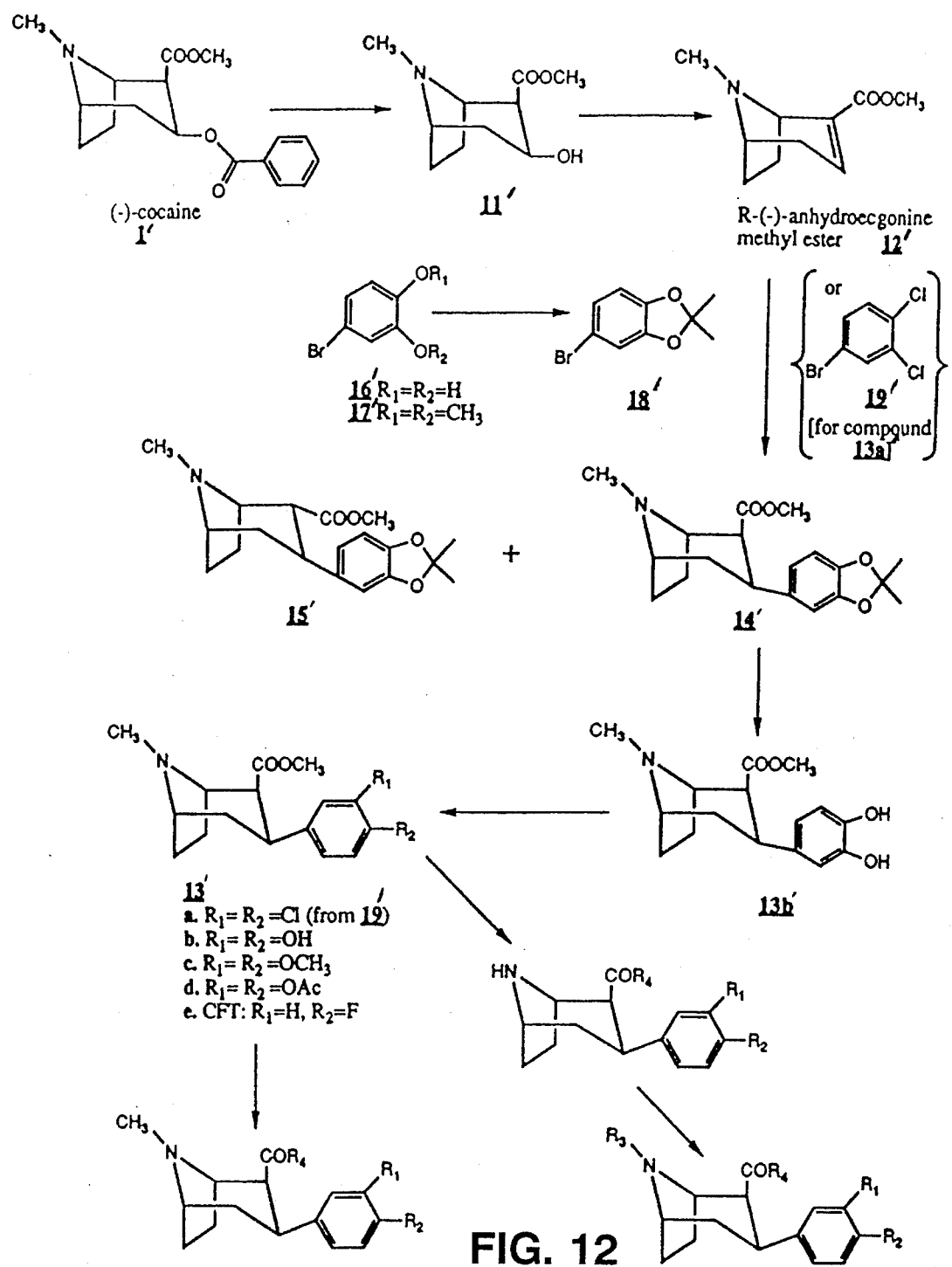

FIG. 12 shows a synthetic scheme for the preparation of 2β-carbomethoxy-3β-phenyltropanes.

Figure 13:
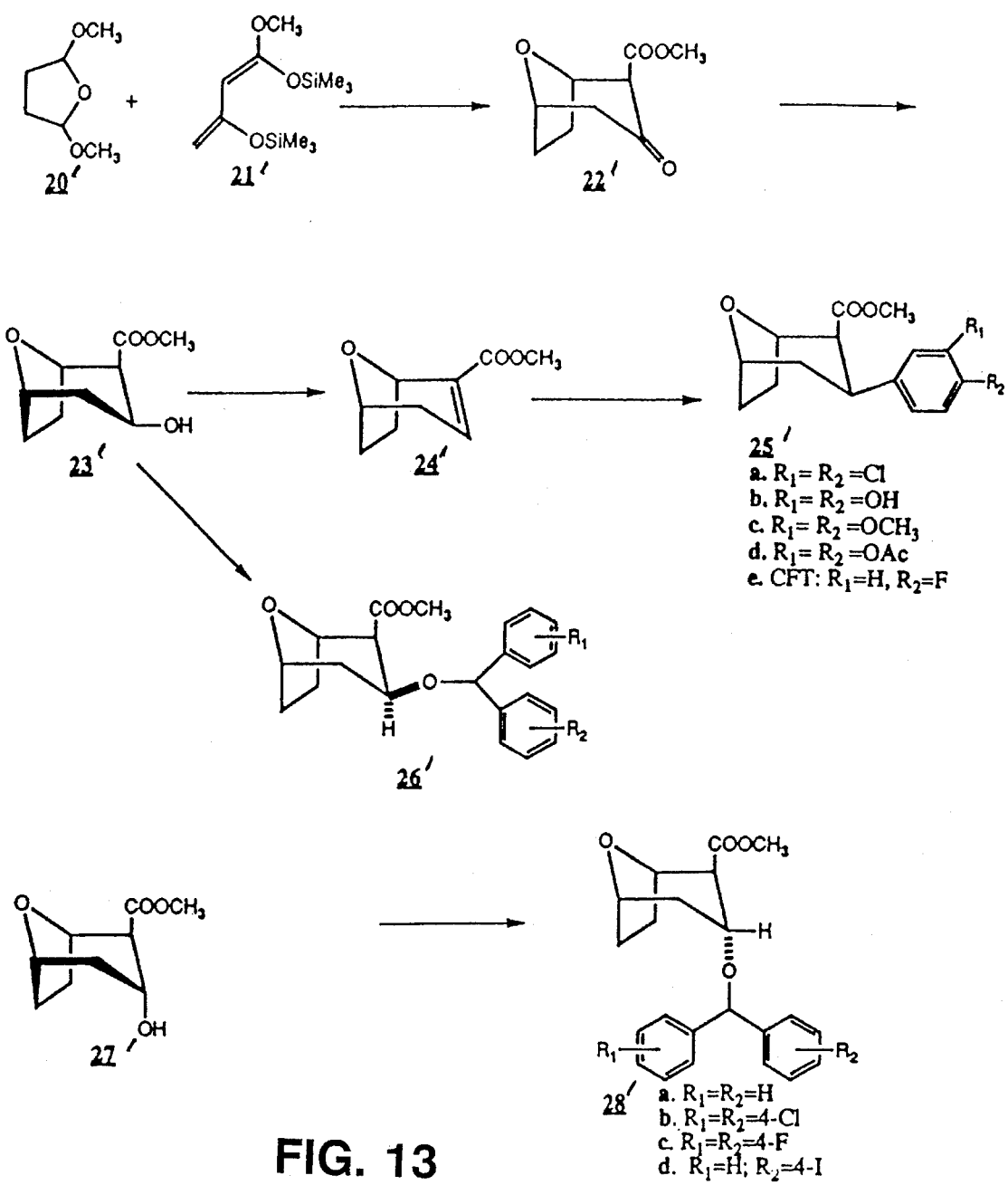

FIG. 13 shows a synthetic scheme for the preparation of analogs of the invention which lack a nitrogen in the tropane ring.

DESCRIPTION OF THE PREFERRED EMBODIMENT

I. EXAMPLES OF COCAINE MIMICS

At various points below, we refer to the ability of cocaine analogs to mimic cocaine binding in the brain, and to mimic the in vivo effects of cocaine. One compound that has been studied in this regard is 2β-carbomethoxy-3β-(4-fluorophenyl)tropane or "CFT"; it is also designated "WIN 35,428". There now follows a description of the ability of CFT to mimic cocaine binding in the brain and also to mimic its effects. There also follows a description of synthetic cocaine analogs which possess higher affinity than CFT for cocaine receptors in the brain and which may therefore be used as cocaine substitutes to treat cocaine addiction and, when detectably labelled, may be used as tags to assay the number of cocaine receptors in the brain. Because such receptors are present in decreased number in the brains of patient's afflicted with Parkinson's disease, such synthetic cocaine analogs facilitate a method of in vivo imaging for diagnosing this disease. In addition, such analogs, by virtue of their ability to inhibit dopamine transport and increase synaptic dopamine levels may serve as therapeutics for Parkinson's disease.

The cocaine receptor-binding assays, and the other protocols for testing the ability of CFT to mimic cocaine, can also be used for evaluating the other cocaine analogs described below. Those skilled in the art will understand that the procedures detailed below for CFT are generally applicable to other cocaine analogs discussed below.

II. CFT AS A PROBE FOR COCAINE RECOGNITION SITES IN THE BRAIN

A. CFT:Cocaine Receptor Binding

In early studies, the binding properties of the cocaine congener [$^3$H]CFT were determined in tissue homogenates and compared with those of [$^3$H]cocaine (Madras et al., Mol. Pharmacol. 36:518–524, 1989). All studies were conducted in monkey brain caudate-putamen for two reasons. First, this dopamine-rich brain region has the highest density of [$^3$H] cocaine receptors in the brain, and dopamine has been implicated in mediating the effects of cocaine. Second, primates are consistently used to test diagnostic imaging agents and to test for cocaine-like drugs and drug therapies for Parkinson's disease. These studies indicated that [$^3$H] CFT and [$^3$H]cocaine binding in monkey caudate-putamen were similar in the following respects:

(1) The density of [$^3$H]CFT binding sites (Bmax: 388 pmol/g) was similar to the density of [$^3$H]cocaine binding sites (Bmax: 471 pmol/g).

(2) Both [$^3$H]cocaine and [$^3$H]CFT labeled high- and low-affinity binding components, with the high-affinity component constituting approximately 10% of the total number of sites.

(3) NaCl was necessary for specific binding of $^3$H]CFT and [$^3$H]cocaine.

(4) Both [$^3$H]CFT and [$^3$H]cocaine were inhibited stereoselectively by the enantiomers of cocaine and pseudococaine and by the diastereoisomers of WIN 35,065-2.

(5) A high positive correlation between the potencies of drugs for inhibiting specifically bound [$^3$H]CFT and [$^3$H]cocaine was clearly demonstrated (0.99; p<0,001; FIG. 1A).

Figure 1B:
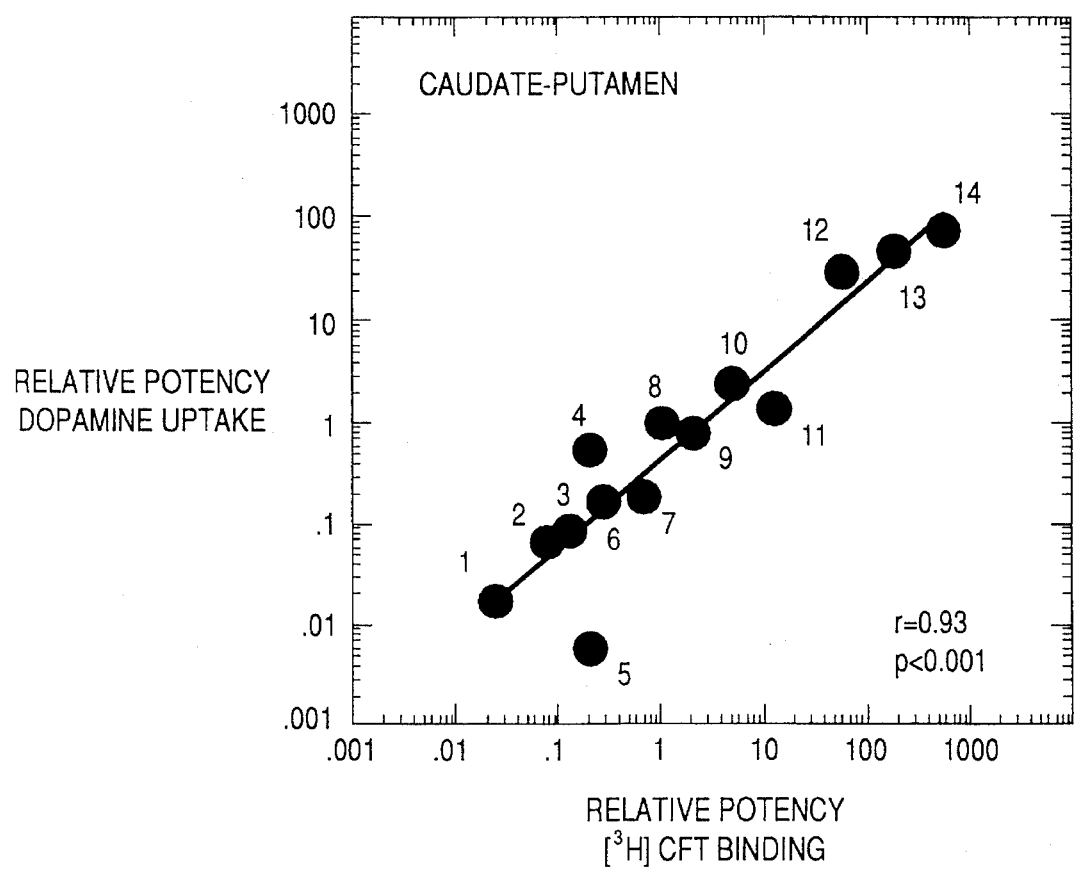
Figure 1C:
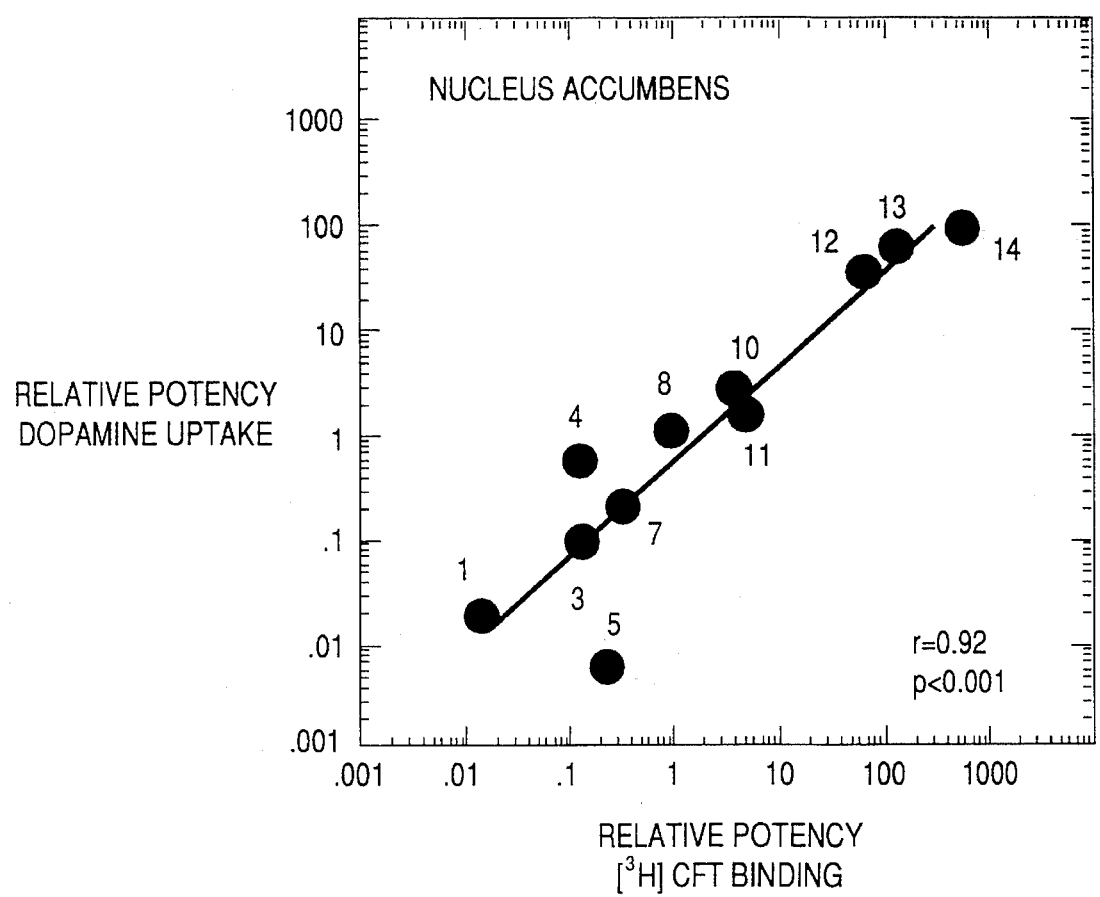
(FIG1C) at the dopamine transporter in the nucleus accumbens.

(6) A high positive correlation was found between the relative potencies of drugs for inhibiting [$^3$H]CFT or [$^3$H]cocaine binding and for inhibiting dopamine uptake (FIG. 1B).

Figure 2A:
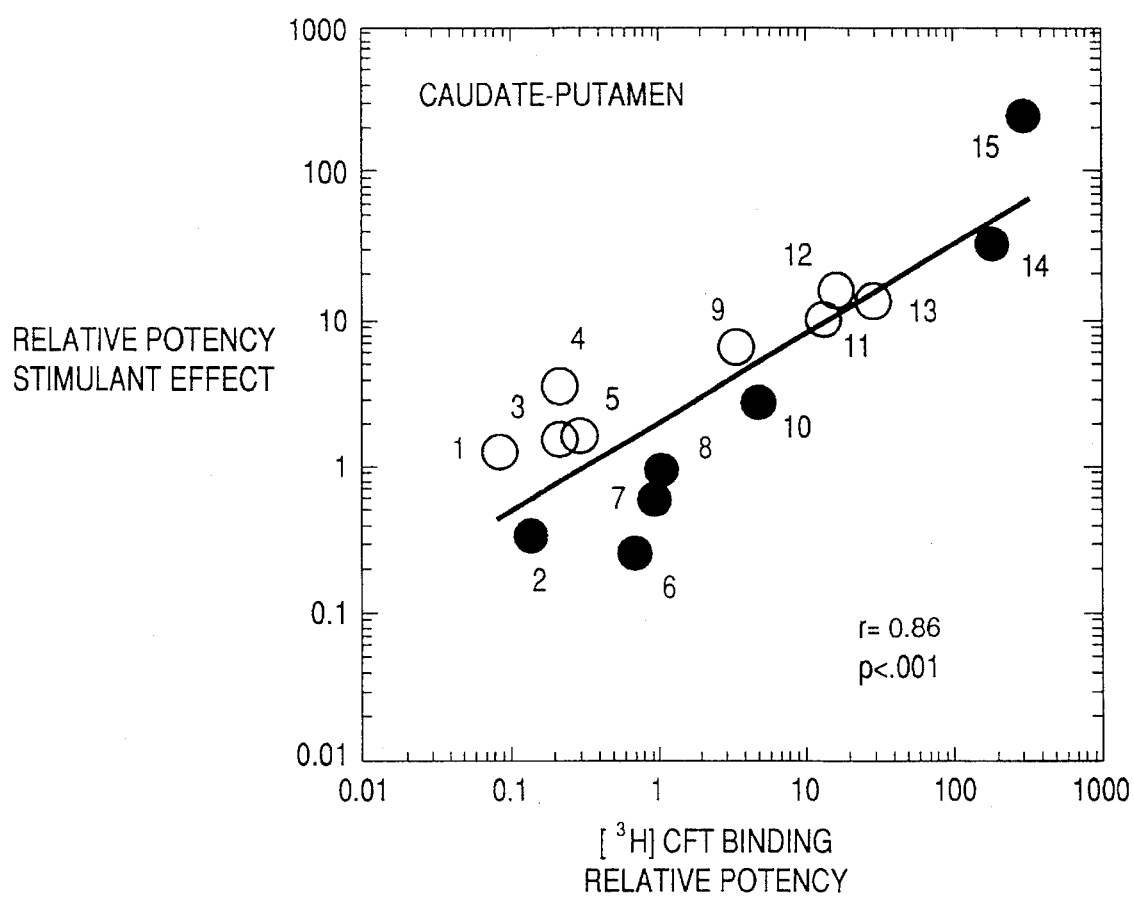
FIGS. 2A and 2B are graphs showing the relationship (FIG. 2A) between [$^3$H]CFT binding and psychomotor stimulation and (FIG. 2B) between [$^3$H]CFT binding and maintenance of drug self-administration.
Figure 2B:
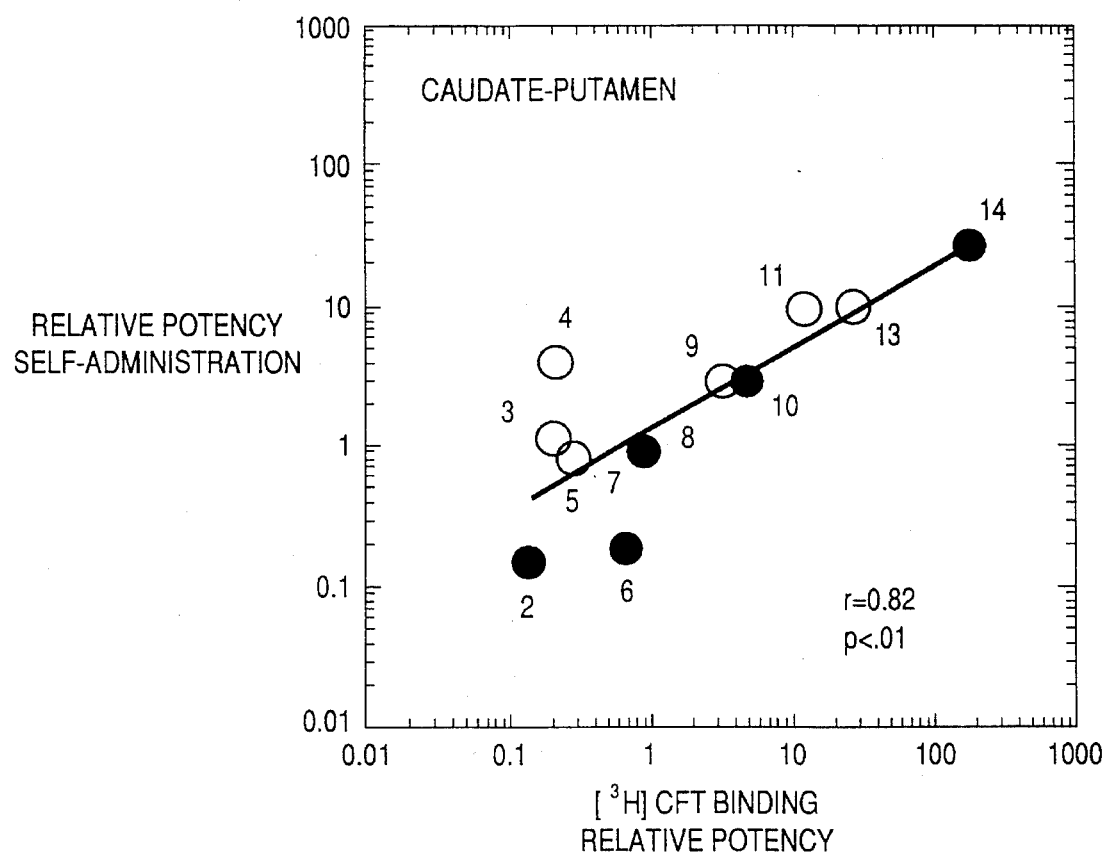

(7) The relative potencies of cocaine analogs and other monoamine uptake inhibitors for inhibiting [3H]CFT binding in monkey caudate-putamen corresponded closely to their relative potencies for producing behavioral stimulation (FIG. 2A) and for maintaining intravenous drug self-administration (FIG. 2B). This high degree of correspondence supports the view that in caudate-putamen, the pharmacological profiles of [$^3$H] CFT and [$^3$H]cocaine are virtually identical and that [$^3$H]CFT labels behaviorally relevant cocaine receptors.

Figure 3:
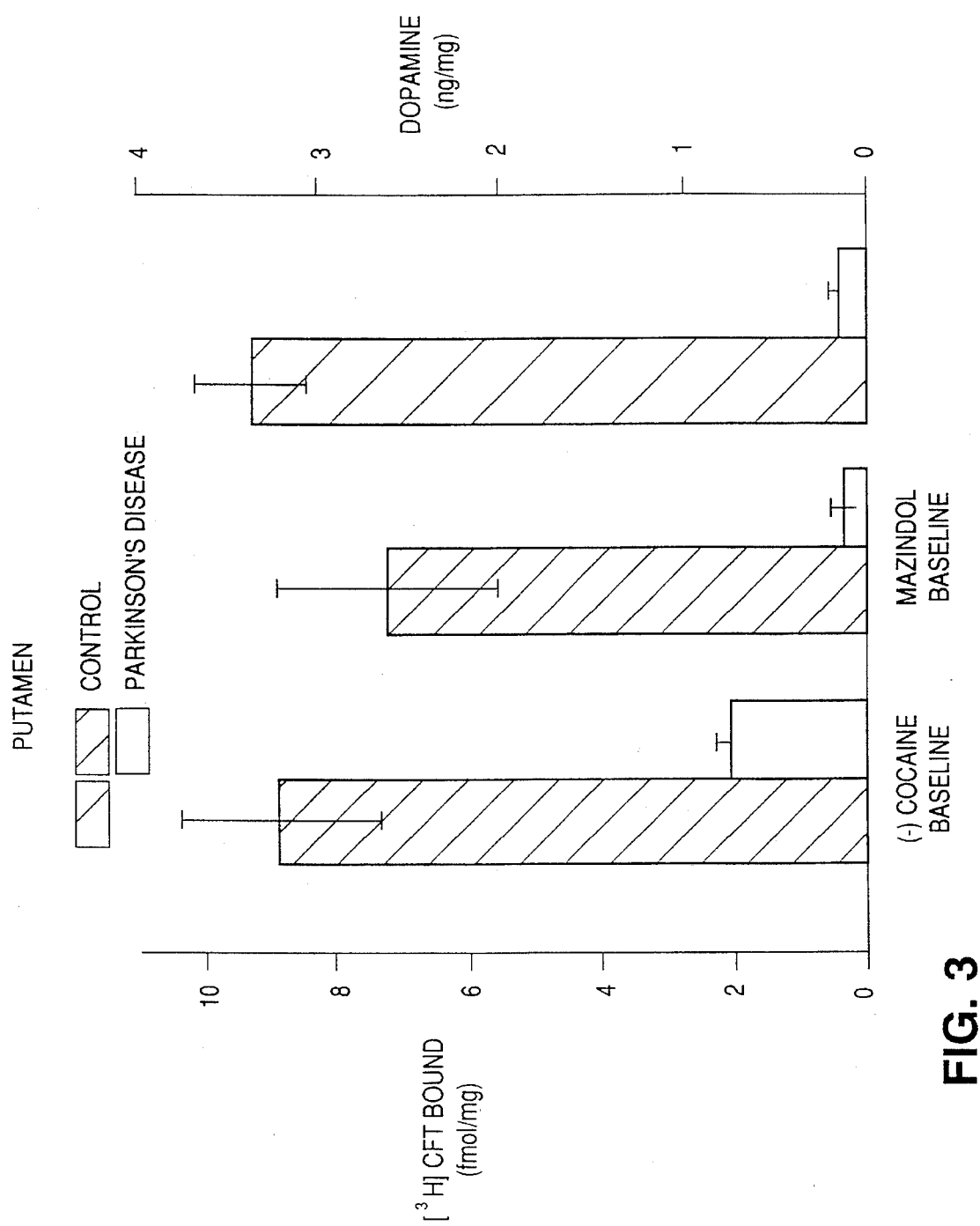
FIG. 3 is a bar graph showing a comparison between the amount of [$^3$H]CFT bound in normal and Parkinson's-diseased human putamen and the relationship to dopamine levels.

Depletion of [$^3$H]cocaine binding sites in postmortem Parkinson's diseased putamen has been attributed to the pre-synaptic location of cocaine binding sites associated with the dopamine transporters (Schoemaker et al., Naunyn-Schmiedeberg's Arch. Pharmacol. 329:227–235, 1985). [$^3$H]CFT binding sites are severely depleted in postmortem human Parkinson's diseased caudate-putamen using either tissue homogenates (FIG. 3) or tissue sections to monitor [$^3$H]CFT binding. These results suggest that CFT is a suitable marker for Parkinson's disease (Madras et al., Soc. Neurosci. Abst. 16:14, 1991; Kaufman and Madras, Synapse 9:43–49, 1991).

Moreover, the affinity of [$^3$H]CFT was higher and its dissociation rate slower than that of [$^3$H]cocaine. Improvements in both parameters were essential for detailed mapping and characterization of cocaine binding sites in the brain. The affinity of [$^3$H]CFT ($K_{0.50}$:16.0 nM) was 18 times higher than that of [$^3$H]cocaine ($K_{0.80}$:283 nM) and the dissociation rate considerably slower. Although unanticipated, [$^3$H]CFT offered other advantages over [$^3$H]cocaine. A higher degree of reproducibility using [$^3$H]CFT enabled previously unrecognized differences in the binding of drugs to become apparent. For example, competition curves for certain cocaine congeners and other drugs (e.g., CFT, cocaine, and (−)-norcocaine) were shallow (0.61–0.89), reached full displacement of [$^3$H]CFT and were characterized by at least two binding components. In contrast, competition curves for monoamine uptake inhibitors structurally distinct from cocaine (e.g., Lu 19-005, GBR 12909 and bupropion) were steeper (0.94–1.1), plateaued at levels corresponding to about 90–93% and were characterized by a single binding component. Furthermore, the level of non-specific binding of [$^3$H]CFT was lower than that of [$^3$H]cocaine. The low level of non-specific binding suggested that [$^3$H]CFT and other radiolabeled forms of CFT would be useful probes for imaging cocaine recognition sites and dopamine terminals and dopamine terminals in vitro and in vivo.

B. Behavioral Effects of CFT

To determine whether CFT also mimicked cocaine's behavioral effects in vivo (specifically the reinforcing and interoceptive effects), squirrel monkeys were trained to respond under a second order schedule of i.v. drug self-administration (see detailed description below). These studies demonstrated that CFT was approximately six times more potent than cocaine in maintaining responding. The potency relationships were similar to the potency relationships for cocaine and CFT for inhibiting [$^3$H]CFT or [$^3$H] cocaine binding and for inhibiting dopamine uptake. The results were consistent with the view that the reinforcing effects of cocaine are mediated by cocaine recognition sites associated with the dopamine uptake system.

The subjective (interoceptive) effects of cocaine were studied in monkeys through the use of a drug discrimination procedure. This procedure was used to determine whether CFT produced a stimulus cue comparable to that of cocaine. Squirrel monkeys were trained to discriminate cocaine (0.3–0.56 mg/kg) from saline using a two-level choice procedure. CFT fully generalized to the cocaine cue, and their potency relationships relative to cocaine corresponded to the potency relationships for inhibiting [$^3$H]CFT binding sites in vitro. These results indicated that the subjective effects of CFT and cocaine were similar again suggesting that [$^3$H]CFT represented a useful probe for characterizing behaviorally relevant cocaine binding sites.

C. Distribution of CFT in Primate Brain

To identify the distribution of cocaine recognition sites in the brain, autoradiographic techniques were utilized. Such techniques were particularly appropriate for this purpose because they are 100–1,000 times more sensitive than radioreceptor assays conducted in tissue homogenates. The moderately high affinity, slow dissociation, and low level of non-specific binding of [$^3$H]CFT made this congener particularly well suited for autoradiography and for imaging.

Three sequential procedures: parametric studies, in vitro autoradiographic techniques, and ex vivo autoradiographic techniques were conducted in tissue sections of squirrel monkey brains. It should be noted that the pharmacological specificity of [$^3$H]CFT binding sites in squirrel monkey and cynomolgus striatum are virtually identical.

In order to characterize binding sites for [$^3$H]CFT in tissue sections, competition experiments were conducted using a fixed concentration of [$^3$H]CFT (3 nM) and a range of concentrations of (−)-cocaine, (+)-cocaine, CFT, Lu 19-005, GBR 12909, bupropion and citalopram. The $IC_{50}$ values for the drugs in tissue sections corresponded closely with their reported $IC_{50}$ values in monkey caudate-putamen membranes (r: 0.99; p<0,001), suggesting that [$^3$H]CFT binding is similar in the two preparations. The pharmacological specificity of [$^3$H]CFT binding sites in substantia nigra and zona incerta were similar.

After establishing suitable conditions for autoradiography, systematic mapping of cocaine recognition sites were conducted in squirrel monkey brain at nine anterior-posterior levels. Tissue sections were incubated alone, or in the presence of excess (−)-cocaine to determine total and non-specific binding of [$^3$H]CFT, respectively. High densities of [$^3$H]CFT binding were present in the dopamine-rich brain regions, including the caudate nucleus, putamen, nucleus accumbens, and olfactory tubercle. In each of these brain regions, specific binding was >90% of total binding. Intermediate densities of [$^3$H]CFT binding were detected in substania nigra, zona incerta, amygdala, and the hypothalamus. Low, though measurable, levels of [$^3$H]CFT binding were observed in the bed nucleus of the stria terminalis, the ventral tegmental area, the medial preoptic area, the pineal, the hippocampus, and the thalamic central nuclei. Near background levels were found in the white matter, cerebellum, globus pallidus, and cortical regions (FIG. 4A). The distribution and density of [$^3$H]CFT binding sites closely paralleled the distribution of $D_1$ and $D_2$ dopamine receptors and the concentration of dopamine in primate brain, mediating the behavioral effects of cocaine (Kaufman et al., Synapse, supra, 1991).

From the in vitro autoradiographic studies, two conclusions were drawn: (a) cocaine receptors labelled by [$^3$H]CFT distributed primarily to dopamine-rich brain regions and (b) the highly circumscribed distribution and low level of non-specific binding of [$^3$H]CFT further supported the development of CFT as a PET imaging ligand for cocaine receptors in vivo. However, as the distribution pattern of a probe in vitro may not necessarily reflect its distribution in vivo, it was necessary to determine whether similar conclusions could be drawn using ex vivo autoradiographic techniques. The ex vivo autoradiographic distribution of [$^3$H]CFT was determined following intravenous administration of [$^3$H]CFT (1.0 or 2.5 nmol/kg) to squirrel monkeys (FIG. 4B). Brain sections from several A-P levels were exposed to [$^3$H]-sensitive film. The resulting autoradiograms revealed binding of [$^3$H] CFT primarily in dopamine-rich brain regions: caudate, putaman>nucleus accumbens/olfactory tubercla, stria terminalis>substantia nigra>hypothalamus. Several regions such as cortex and thalamus displayed more prominent binding in vivo than in vitro. Nevertheless, the ex vivo labeling of brain regions by [$^3$H]CFT corresponded closely to the in vitro autoradiographic pattern.

At the time these studies were completed, a higher affinity iodinated analog of [$^3$H]CFT, [$^{125}$I]RTI-55 (i.e., CIT, 2β-carbomethoxy-3β-(4-iodophenyl)tropane; Dupont-NEN), became available. [$^{125}$I] RTI-55 labels sites in the caudate putamen with an approximately 10 fold higher potency than

[³H]CFT. This ligand was also tested by ex vivo autoradiography as an imaging probe. Experiments carried out as described above revealed that highest densities of [$^{125}$I]RTI-55 were detected in the caudate-putamen, and moderately high densities also were found in the thalamus, cortex and brain stem nuclei. The results indicated that although both probes labeled dopamine-rich brain areas, [$^{125}$I]RTI-55 labeled sites in addition to those recognized by [³H]CFT. The additional sites labeled by [$^{125}$I]RTI-55 are associated with the serotonin transporter (Kaufman et al., Soc. Neurosci. Abst., 1991).

D. CFT as a PET Imaging Probe

In a collaborative study with the PET imaging group at the Massachusetts General Hospital, a PCR-I camera was used to conduct preliminary PET imaging studies with [$^{11}$C]CFT in cynomolgus and squirrel monkeys in order to determine the distribution and kinetic properties of the ligand. The monkeys were injected with [$^{11}$C]CFT (Sp. act.: 400–700 Ci/mmol, 3–9 μg, 0.5–1 ml), arterial blood samples were collected, and dynamic imaging was carried out for 90 minutes. Images showed high uptake of [$^{11}$C]CFT in the caudate-putamen with a resulting striatal-to-cerebellar ratio of >4.0 at 58 min. Mazindol and other dopamine uptake inhibitors displaced bound [$^{11}$C]CFT from the striatum. [$^{11}$C]CFT binding was reduced in MPTP-treated Parkinsonian monkeys and depletion was found in asymptomatic monkeys. These results further suggest the use of [$^{11}$C]CFT to monitor Parkinson's disease (Hantraye et al., Neuro. Reports 3:265–268, 1992).

E. CFT Binding in Human Brain

Results from the PET imaging studies were sufficiently encouraging to support further evaluation of CFT as a potential imaging probe for human brain. In order to determine whether [³H]CFT labels sites associated with the dopamine transporter, the binding of [³H]CFT to homogenates of human caudate nucleus and putamen, was characterized. [³H]CFT binding was saturable, stereoselective, and inhibited by drugs with a rank order of potency: Lu 19-005>CFT, mazindol, GBR 12909>(−)-cocaine>bupropion>(+)-cocaine, that was identical with that of cocaine receptors associated with the dopamine transporter in monkey caudate-putamen.

III. NOVEL COCAINE ANALOGS

The modest affinity of CFT and its selectivity for the dopamine transporter motivated the development of cocaine congeners with improved properties for use as imaging probes; desirable properties included high affinity and high selectivity for the dopamine transporter (preferably in the picomolar-low nanomolar range). The affinity and selectivity of the congener is preferably at least comparable to that of cocaine so that the full spectrum of biologically relevant cocaine recognition sites throughout the brain may be monitored. The compounds of the invention are examples of such improved imaging probes.

Another object of the invention was to develop compounds useful for cocaine drug therapy. Such compounds include cocaine-like drugs preferably having a longer onset time, a longer duration of action, and a diminished abuse liability relative to cocaine; compounds described herein are expected to have such properties. The need also exists for cocaine antagonists which preferably bind sites normally bound by cocaine but without inhibiting dopamine transport. The compounds of the invention which lack a ring nitrogen or possess a catechol moiety likely provide such useful cocaine antagonists. A number of the compounds described herein are useful for the treatment of Parkinson's disease and similar neurodegenerative disorders.

There now follows a description of the synthesis of compounds of the invention.

A. Benztropines, In General

Cocaine, and CFT (WIN 35,428) both have the C-3 substituent in the β configuration, in contrast to benztropine's 3α-diphenylmethoxy group. In the case of benztropine, the α-orientation of the C-3 substituent appears to increase activity. This finding is surprising in view of reports of substantial loss of activity in the cocaine series when the 3-phenyl ester is switched from the β- to the α-configuration.

As shown in FIGS. 5, benztropine is a 3α-diphenylmethoxytropane analog of cocaine. It is unsubstituted in the C-2 position and therefore not optically active. In general, introduction of a carbomethoxy group at C-2 of the 3α-benztropine molecule can further enhance binding. Without wishing to bind ourselves to a specific theory, it appears that the resulting molecules more closely mimic the structural features of both cocaine and CFT. Introduction of such a functionality at the C-2 position of the benztropine confers optical isomerism and generates eight regio and optical isomers. The cocaine series, including all the tropanes analogous to CFT, is of the R-configuration. Surprisingly, we have found S-enantiomers of C-2 substitued cocaine analogs (particularly those having a bulky hydrophobic C-3α substituent) are important. The (S)-(+)-2β-carbomethoxy-3α-(disubstituted phenylmethoxy)tropanes are particularly of interest.

Synthesis schemes for the eight representative regio and optical isomers are described below. Those skilled in the art will recognize that these synthetic schemes can be generally applied to analogs of the isomers.

1. General Synthetic Strategies;

a. 2-Carbomethoxy-3-diphenylmethoxytropanes

The series is prepared by total synthesis from 3-tropinone. An efficient route to RS-2 (FIG. 6) has been described (Carroll, F. I. et al., *J. Med. Chem.*, 34, 883, 1991).(see FIG. 6). Specifcally, FIG. 7 shows synthesis of the 4 R-enantomers (R9, R7, R10, AND R8), and FIG. 8 shows synthesis of the 4 S-enantomers (S9, S7, S10, AND S8).

As shown in FIG. 6, commercially available 3-tropinone (1) is reacted with dimethyl carbonate (Lewin, A. H., Naseree, T., and Carroll, F. I., *J. Het. Chem.*, 24, 19, 1987; Carroll, F. I., Coleman, M. L., and Lewin, A. H., *J. Org. Chem.*, 47, 13, 1982.) to provide (+)-2-carbomethoxy-3-tropinone, 2 which is resolved by standard means (Carroll, F. I., Lewin, A. H., Abraham, P., Parham, K., Boja, J. W., and Kuhar, M. J., *J. Med. Chem.*, 34, 883, 1991) by crystallization of the bitartrates from either (−)-tartaric acid to obtain (S)-(−)-2-carbomethoxy-3-tropinone S-2, or (+)-tartaric acid to obtain the (R)-(+)-2-carbomethoxy-3-tropinone, R-2. The optical rotations of the products are then compared with the literature values.

Reduction of each of the resolved enantiomerically pure tropinones 2 to provide the six 2-carbomethoxy-3-hydroxy compounds, (R)- and (S)-3, 4, and 5, is effected with sodium borohydride in methanol at low temperature. Epimerization at C-2 to obtain the desired β-carbomethoxy epimers occurs with concurrent hydrolysis upon reflux with water. The methyl esters are then reintroduced, without epimerization, by means of methanol and HCl, to obtain the target intermediates (R)- and (S)-6. Compounds 3, 4, 5, and 6 are then treated with the appropriately substituted benzhydrol to obtain the desired benztropines, (R)- and (S)-7, 8, 9, and (R)-2β-Carbomethoxy-3β-diphenylmethoxytropanes are prepared by reaction of the appropriate benzhydrol with ecgonine methyl ester. Ecgonine methyl ester is prepared in quantitative yield from (−)-cocaine by sequential hydrolysis, dehydration with $POCl_3$, and Fischer esterification with MeOH. It should be noted that resolution is not required in this instance since all stereochemistry is controlled by the starting material (−)-cocaine. Examples of representative experimental procedures follow.

b. 2β-Carbomethoxy-3α-diphenylmethoxytropanes (3')

As shown in FIG. 10, commercially available 3-tropinone (5') is reacted with dimethyl carbonate (Lewin et al., J. Het. Chem. 24:19,1987; Carroll et al., J. Org. Chem. 47:13,1982) to provide (+)-2β-carbomethoxy-3-tropinone (6') which, in turn, requires careful resolution of the racemic mixture. Carroll (J. Med. Chem. 34:883, 1991) has achieved this separation in reasonable yield via sequential selective crystallization of the bitartrate from (−)-tartaric acid to obtain (S)-2-carbomethoxy-3-tropinone, followed by crystallization with (+)-tartaric acid to obtain the desired (R)-2-carbomethoxy-3-tropinone (7'). Crystallization may be carried out with (+)-tartaric acid to obtain the (R)-enantiomer directly. The optical rotation of this product, as its bitartrate salt as well as free base, is measured and compared with literature values (Carroll et al., J. Med. Chem. 34:883, 1991).

Reduction of the resolved enantiomerically-pure tropinone (7') to provide the 2e-carbomethoxy-3α-hydroxy compound, (R)-allopseudoecgonine methyl ester (8') is effected with sodium borohydride in methanol at low temperature. Epimerization at C-2 to obtain the desired β-carbomethoxy epimer occurs with concurrent hydrolysis upon reflux with water to provide 9'. The methyl ester is then reintroduced, without epimerization, by means of methanol and HCl, to obtain the target intermediate, (R)-alloecgonine methyl ester (10').

Compound 10' is treated with the appropriately substituted diaromatic diazomethane to obtain the desired benztropines (3') (Phillips, U.S. Pat. No. 2,595,405, 1952). See FIG. 10.

An alternative synthetic route to 3' is described in FIG. 11. In that route, (−)-cocaine is hydrolyzed to 11' and oxidized to preovide the ketone 7' which is hten converted to enantiomerically pure 3'.

To synthesize the R-configuration of 3α- and 3β-analogs, the schemes shown in FIGS. 10-12 are followed. The α-series is prepared from compound 10. An efficient route to 10 is that recently described by Carroll et al. (J. Med. Chem. 34:883, 1991) (see FIG. 10). An alternate route to the a-series compounds 3 is shown in the scheme depicted in FIG. 11. While the synthetic route represented in FIG. 10 requires optical resolution, the route represented in FIG. 11 does not. The β-configured compound is obtained from ecgonine methyl ester, 11, (FIG. 13) which is readily available from (−)-cocaine, 1.

FIGS. 11 and 12 illustrate alternatives to the synthetic routes for the preparation of 2β-carbomethoxy-3α-diphenylmethoxytropanes described above and illustrated in FIG. 5A.

According to one alternative shown in FIG. 11, Compound 10' is treated with the appropriately substituted diaromatic diazomethane to obtain the desired benztropines (3') (Phillips, U.S. Pat. No. 2,595,405, 1952). Compounds 3a'–3e' (FIG. 5A) are synthesized by this route.

In still another alternative synthetic route, (−)cocaine is hydrolyzed to 11 and oxidized to provide the ketone 7 which is then converted to enantiomerically pure 3.

What follows are specific examples of the above synthetic schemes.

(RS)-(+)-2-Carbomethoxy-3-tropinone (RS-2)

3-Tropinone, 1, (20.59 g, 0,148 mole) in cyclohexane (140 mL) was added dropwise to a mixture of NaH (60% dispersion, 11.83 g, 0.296 mol), dimethylcarbonate (27.4 mL, 0.325 mole) and cyclohexane (60 mL), at gentle reflux. MeOH (0.5 mL) was added at end of addition. The reaction mixture was heated at reflux until effervesence ceased. Water (250 mL) was added after the reaction mixture was cooled to room temperature. The layers were separated and the cyclohexane layer was extracted with additional water (2×100 mL). The combined aqueous layers were saturated with $NH_4Cl$ (120 g) and extracted with $CH_2Cl_2$ (8×100 mL). The dried ($K_2CO_3$) extracts were concentrated to dryness to afford 23.1 g (79%) of RS-2 as a yellowish oil which crystallized upon standing. The material was purified by flash chromatography (10% $iPrNH_2$, 30% $Et_2O$/hexane) to afford 20 g of RS-2: mp 102°–103° C.; $R_f$ 0.65 ($CH_2Cl_2$/$CHCl_3$/MeOH/$NH_4OH$ 100:40:9:1 two elutions).

Resolution of (RS)-2-Carbomethoxy-3-tropinone (RS-2)

(R)-(+)-2-Carbomethoxy-3-tropinone (R-2)

L-Tartaric acid (9.0 g, 0.06 mole) was added to (RS)-2-carbomethoxy-3-tropinone, RS-2, (11.61 g, 0.059 mole) in EtOH (100 mL). EtOH was removed in vacuo after all the tartaric acid had dissolved. The residue was recrystallized once from a 10:1 acetone-water (440 mL) mixture (19.68 g of material obtained) and once from MeOH (100 mL) to afford 6.21 g (30%) of (R)-2-carbomethoxy-3-tropinone (+)-hydrogen tartrate as a white crystalline solid. The salt was disssolved in saturated $Na_2CO_3$ (50 mL) and the free base generated was extracted with $CH2Cl_2$ (2×100 mL). The dried ($K_2CO_3$) extracts were concentrated to afford 3.56 g of (R)-2-carbomethoxy-3-tropinone, R-(+)-2, as a white solid: mp 104°–106° C.; $R_f$ 0.65 ($CH_2Cl_2$/$CHCl_3$/MeOH/$NH_4OH$ 100:40:9:1 two elutions): $[a]^{21}D$ +18.6 (c=1, MeOH) [lit $[a]^{25}D$ +25.4° (c=1, MeOH) (Carroll et al. J. Med. Chem. 1991, 34, 884]; $[a]^{20}_D$+18.3° (c=1, MeOH) Findlay J. Org. Chem. 1957, 22, 1385)]

(S)-(−)-2-Carbomethoxy-3-tropinone (S-2)

The filtrates from above were concentrated to dryness. The residue obtained was dissolved in saturated $Na_2CO_3$ (50 mL) and the free base generated was extracted with $CH_2Cl_2$ (100 mL). The dried ($K_2CO_3$) organic extract was concentrated to dryness. The residue (2.37 g, 0,012 mol) and D-tartaric acid (2.6 g, 0,017 mol) were dissolved in EtOH. EtOH was then removed in vacuo and the residue was recrystallized once from a 10:1 acetone-water (110 mL) mixture (3.7 g obtained) and once from MeOH (20 mL) to afford 2.15 g of (S)-2-carbomethoxy-3-tropinone (−)-hydrogen tartrate. The free base, S-(−)-2, was generated as above (1.1 g): mp 104°–105° C.; $R_f$ 0.65 ($CH_2Cl_2$/$CHCl_3$/MeOH/$NH_4OH$ 100:40:9:1 two elutions): $[a]^{21}_D$ −18.5° (c=1, MeOH) [lit $[a]^{25}_D$ −25.7° (c=1, MeOH) (Carroll et al J. Med. Chem. 1991, 34, 884); $[a]^{21}_D$ −18.3° (c=1, MeOH) (Findlay J. Org. Chem. 1957, 22, 1385)]

(R)-Ecgonine methyl ester (R-3)

(R)-Pseudoecgonine methyl ester (R-4)

(R)-Allopseudoecgonine methyl ester (R-5)

$NaBH_4$ (1.55 g, 0.041 mol) was added to a solution of (R)-2-carbomethoxy-3-tropinone, R-2, (3.4 g, 017 mol) in MeOH (300 mL) at −78° C. The reaction mixture was left in the freezer (−30° C.) overnight. Conc. HCl (8 mL) was added carefully and the solution was concentrated to dryness. The residue was dissolved in water (100 mL), basified with NH$_4$OH, saturated with NaCl and extracted with CH$_2$Cl$_2$ (3×100 mL). The dried (K$_2$CO$_3$) extracts were concentrated to dryness (3.1 g). The residue was chromatographed over silica gel (CH$_2$Cl$_2$/CHCl$_3$/MeOH/NH$_4$OH 100:40:9:1) to afford (R)-ecgonine methyl ester, R-3, (120 mg, 3.5%), as a yellow oil: R$_f$ 0.69 (CH$_2$Cl$_2$/CHCl$_3$/MeOH/NH$_4$OH 100:40:9:1 two elutions).

(R)-pseudoecgonine methyl ester, R-4, (590 mg, 17%): R$_f$ 0.33 (CH$_2$Cl$_2$/CHCl$_3$/MeOH/NH$_4$OH 100:40:9:1 two elutions). and (R)-allopseudoecgonine methyl ester, R-5, (2.25 g, 66%) R$_f$ 0.25 (CH$_2$Cl$_2$/CHCl$_3$/MeOH/NH$_4$OH 100:40:9:1 two elutions).

(R)-Alloecgonine methyl ester (R-6)

(R)-Allopseudoecgonine methyl ester, R-5, (1.68 g) and water (25 mL) were combined and heated at reflux for 18 h. Water was removed. Methanolic HCl (100 mL) was added and stirred at room temperature overnight. The reaction mixture was concentrated to dryness. The residue was dissolved in water (100 mL), basified with NH$_4$OH and extracted with CH2Cl$_2$ (150 mL). The dried (K$_2$CO$_3$) extract was concentrated to dryness. The residue was chromatographed over silica gel (3% NH4OH, 5% MeOH in EtOAc) to afford (R)-alloecgonine methyl ester, R-6, (0.80 g, 48%): R$_f$ 0.54 (5% MeOH/EtOAc+NH$_4$OH), anhydroecgonine methyl ester (45 mg) and starting material, R-5, (350 mg, 21%).

(R)-(–)-2β-Carbomethoxy-3α-(di-4-fluorophenyl-methoxy)tropane (R-8)

(R)-Alloecgonine methyl ester, R-8, (173 mg, 0.87 mmol), 4,4'-difluorobenzhydrol (382 mg, 1.74 mmol), p-toluenesulfonic acid monohydrate (200 mg, 1.04 mmol) and benzene (50 mL) in a 100 mL round bottom flask fitted with a Dean-Stark trap and condenser was heated at reflux for 18 h. 4,4'-Difluorobenzhydrol (320 mg) and p-toluenesulfonic acid monohydrate (70 mg) were added and the reaction mixture was heated at reflux for a further 5 h. Benzene was removed in vacuo. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 2% MeOH in EtOAc) to afford (R)-(–)-2b-carbomethoxy-3a-(di-4-fluorophenylmethoxy)tropane, R-8, (283 mg, 81%) as a white solid: mp 132°–133° C.; R$_f$ 0 72 (5% MeOH/EtOAc+NH$_4$OH); [a]$^{21}_D$ –18.9 (c=1, MeOH). Anal. (C$_{23}$H$_{25}$NO$_3$F$_2$) C, H, N.

(R)-(–)-2α-Carbomethoxy-3α-(di-4-fluorophenyl-methoxy)tropane (R-10)

(R)-Allopseudoecgonine methyl ester, R-5, (330 mg, 1.7 mmol), 4,4'-difluorobenzhydrol (774 mg, 3.5 mmol), p-toluenesulfonic acid monohydrate (405 mg, 2.1 mmol) and benzene (50 mL) in a 100 mL round bottom flask fitted with a Dean-Stark trap and condenser were heated at reflux for 18h. 4,4'-Difluorobenzhydrol (400 mg) and p-toluenesulfonic acid monohydrate (50 mg) were added and the reaction mixture was heated at reflux for another 5 h. Benzene was removed in vacuo. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 2% MeOH in EtOAc) to afford (R)-(–)-2a-carbomethoxy-3a- (di-4-fluorophenylmethoxy)tropane, R-10, (554 mg, 83%) as a pale yellow viscous oil: R$_f$ 0.42 (10% MeOH/EtOAc+NH$_4$OH); HCl salt mp: 118°–120° C.; [a]$^{21}_D$ –29.0° (c=1, MeOH); Anal. (C$_{23}$H$_{25}$NO$_3$F$_2$.HCl.H$_2$O) C, H, N, Cl.

(R)-(–)-2α-Carbomethoxy-3β-(di-4-fluorophenyl-methoxy)tropane (R-7)

(R) -Pseudoecgonine methyl ester, R-4, (220 mg, 1.1 mmol), 4,4'-difluorobenzhydrol (442 mg, 2.0 mmol), p-toluenesulfonic acid monohydrate (384 mg, 2.0 mmol) and benzene (40 mL) in a 100 mL round bottom flask fitted with a Dean-Stark trap and condenser was heated at reflux for 6 h. 4,4'-Difluorobenzhydrol (440 mg) and p-toluenesulfonic acid monohydrate (50 mg) were added and the reaction mixture was heated at reflux for another 16 h. Benzene was removed. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 10% MeOH in EtOAc) to afford (R)-(–)-2a-carbomethoxy-3b-(di-4-fluorophenylmethoxy)tropane, R-7, (439 mg, 99%) as a pale yellow viscous oil which was treated with ethereal HCl to afford 421 mg (87%) of HCl salt as a white solid: mp.193°–195° C.; R$_f$ 0.67 (5% MeOH/EtOAc+NH$_4$OH); Anal. (C$_{23}$H$_{25}$NO$_3$F$_2$.HCl) C, H, N, Cl.

(R)-(–)-2β-Carbomethoxy-3β- (di-4-fluorophenyl-methoxy)tropane (R-9)

(R)-Ecgonine methyl ester (from natural (R)-cocaine), R-3, (200 mg, 1.0 mmol), 4,4'-difluorobenzhydrol (442 mg, 2 mmol), p-toluenesulfonic acid monohydrate (384 mg, 2.0 mmol) and benzene (40 mL) in a 100 mL round bottom flask fitted with a Dean-Stark trap and condenser were heated at reflux for 6 h. 4,4'-Difluorobenzhydrol (400 mg) and p-toluenesulfonic acid monohydrate (50 mg) were added and the reaction mixture was heated at reflux for another 16 h. Benzene was removed. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (EtOAc:hexane::1:1, EtOAc, 10% MeOH/EtOAc) to afford (R)-(–)-2b-carbomethoxy-3b-(di- 4-fluorophenylmethoxy)tropane, R-9, (146 mg, 36%) as a pale yellow viscous oil which was treated treated with ethereal HCl to afford the HCl salt: mp 120°–123° C.; R$_f$ 0.74 (5% MeOH/EtOAc+ NH$_4$OH); [a]$^{21}_D$ –102.3° (c=1, MeOH). Anal. (C$_{23}$H$_{25}$NO$_3$F$_2$.HCl.1.5 H$_2$O) C, H, N, Cl.

(S) -Ecgonine methyl ester (S-3)

(S) -pseudoecgonine methyl ester (S-4)

(S)-Allopseudoecgonine methyl ester (S-5)

NaBH$_4$ (0.5 g, 13.2 mmol) was added to a solution of (S)-2-carbomethoxy-3-tropinone S-2, (1.09 g, 5.5 mmol) in MeOH (100 mL) at –78° C. The reaction mixture was left in the freezer (-30° C) overnight. Concentrated HCl (3 mL) was added carefully and the solution was concentrated to dryness. The residue was dissolved in water (30 mL), basified with NH$_4$OH, saturated with NaCl and extracted with CH$_2$Cl$_2$ (3×50 mL). The dried (K$_2$CO$_3$) extracts were concentrated to dryness (3.1 g). The residue was chromatographed over silica gel (CH$_2$Cl$_2$/CHCl$_3$/MeOH/NH$_4$OH 100:40:9:1) to afford (S)-ecgonine methyl ester, S-3, as a yellow oil (15 mg, 1.3%); R$_f$ 0.69 (CH$_2$Cl$_2$/CHCl$_3$/MeOH/NH$_4$OH 100:40:9:1 two elutions). (S)-pseudoecgonine methyl ester, S-4, (214 mg, 19%) as an off-white solid: mp 105°–107° C.; R$_f$ 0.33 (CH$_2$Cl$_2$/CHCl$_3$/MeOH/NH$_4$OH 100:40:9:1 two elutions). (S)-allopseudoecgonine methyl ester, S-5, (768 mg, 70%) as an off-white solid, mp 75.5°–77 5° C.; R$_f$ 0.25 (CH$_2$Cl$_2$/CHCl$_3$/MeOH/NH$_4$OH 100:40:9:1 two elutions).

(S)-Alloecgonine methyl ester (S-6)

(S)-Allopseudoecgonine methyl ester, S-5, (0.43 g) and water (10 mL) were combined and heated at reflux for 18 h.

Water was removed in vacuo. Methanolic HCl (25 mL) was added and the mixture stirred at room temperature overnight. The reaction mixture was concentrated to dryness. The residue was dissolved in water (10 mL), basified with NH$_4$OH and extracted with CH$_2$Cl$_2$ (50 mL). The dried (K$_2$CO$_3$) extract was concentrated to dryness. The residue was chromatographed over silica gel (3% NH$_4$OH, 5% MeOH in EtOAc) to afford (S)-alloecgonine methyl ester, S-6, (235 mg, 55%): mp 76.5°–77.5° C.; R$_f$ 0.54 (5% MeOH/EtOAc+NH$_4$OH), and starting material, S-5, (135 mg, 31%).

(S)-(+)-2α-Carbomethoxy-3β-(di-4-fluorophenylmethoxy)tropane (S-7)

(S)-Pseudoecgonine methyl ester, S-4, (94 mg, 0.47 mmol), 4,4'-difluoro-benzhydrol (208 mg, 0.94 mmol), p-toluenesulfonic acid monohydrate (181 mg, 0.94 mmol) and benzene (40 mL) in a 100 mL round bottom flask fitted with a Dean-Stark trap and condenser were heated at reflux for 22h. Benzene was removed. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 5% MeOH in EtOAc) to afford (S)-(+)-2a-carbomethoxy- 3a-(di-4-fluorophenylmethoxy)tropane, S -7, (162 mg, 86%) as a pale yellow viscous oil; R$_f$ 0.67 (5% MeOH/EtOAc+NH$_4$OH). HCl salt mp: 202°–203° C. [a]$^{21}_D$ –20.2° (c=1, MeOH). Anal. (C$_{23}$H$_{25}$NO$_3$F$_2$.HCl.0.2 H$_2$O) C, H, N, Cl.

(S)-(+)-2β-Carbomethoxy-3α- (di-4-fluorophenylmethoxy)tropane (S-8)

(S)-Alloecgonine methyl ester, S-6, (200 mg, 1.0 mmol), 4,4'-difluoro-benzhydrol (442 mg, 2.0 mmol), p-toluenesulfonic acid monohydrate (384 mg, 2.0 mmol) and benzene (40 mL) in a 100 mL round bottom flask fitted with a Dean-Stark trap and condenser was heated at reflux for 18 h. Benzene was removed in vacuo. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (2% NH$_4$OH, 2% MeOH in EtOAc, 5% MeOH, 3% NH$_4$OH in EtOAc) to afford (S)-(+)-2β-carbomethoxy-3α-(di-4-fluorophenylmethoxy)tropane, S-8, (110 mg, 27%) as a off white solid; mp 131°–132° C.; R$_f$ 0.72 (5% MeOH/EtOAc+NH$_4$OH). [a]$^{21}_D$ +21.6° (c=1, MeOH). Anal (C$_{23}$H$_{25}$NO$_3$F$_2$) C, H, N (S)-(+)-2β-Carbomethoxy-3β- (di-4-fluorophenylmethoxy)tropane (S-9)

(S)-Ecgonine methyl ester, S-5, (0.32 g, 1.6mmol), 4,4'-difluorobenzhydrol (0.7 g, 3.2 mmol), p-toluenesulfonic acid monohydrate (0.46 g, 2.4 retool), and benzene (50 mL) in a 100 mL round bottom flask fitted with a Dean-Stark trap and condenser were heated at reflux for 18 h. 4,4'-Difluorobenzhydrol (0.35 g, 1.5 mmol), and p-toluenesulfonic acid monohydrate (60 mg, 0.3 mmol) were added and the reaction mixture was heated at reflux for another 5 h. Benzene was removed in vacuo. The residue was dissolved in water (10 mL), basified with NH$_4$OH and extracted with CH$_2$Cl$_2$ (2×50 mL). The dried (K$_2$CO$_3$) organic extracts were concentrated to dryness. The residue was chromatographed over silica gel (3% NH$_4$OH, 2% MeOH in EtOAc) to afford (S)(+ (+)-2β-carbomethoxy-3β-(di-4-fluorophenylmethoxy)tropane, S-9, (302 mg), as an off-white solid: mp 89°–91° C.; R$_f$ 0.56 (10% Et$_3$N/Et$_2$O); Anal. (C$_{23}$H$_{25}$NO$_3$F$_2$.HCl.0.2 H$_2$) C, H, N, Cl.

(S)-(+)-2α-Carbomethoxy-3α-(di-4-fluorophenylmethoxy)tropane (S-10)

(S)-Allopseudoecgonine methyl ester, S-5, (204 mg, 1.02 mmol), 4,4'-difluorobenzhydrol (451 mg, 2.04 mmol), p-toluenesulfonic acid monohydrate (244 mg, 1.22 mmol) and benzene (50 mL) in a 100 mL round bottom flask fitted with a Dean-Stark trap and condenser was heated at reflux for 18 h. 4,4'-Difluorobenzhydrol (450 mg) was added and the reaction mixture was heated at reflux for a further 8 h. Benzene was removed in vacuo. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 2% MeOH in EtOAc) to afford (S)-(+)-2α-carbomethoxy-3α-(di- 4-fluorophenylmethoxy)tropane, S-10, (234 mg, 57%) as a pale yellow viscous oil: Rf 0.39 (5% MeOH/EtOAc+NH$_4$OH); HCl salt mp: 128°–130° C.; [a]$^{21}_{D+}$19.0° (c=1, MeOH). Anal. (C$_{23}$H$_{25}$NO$_3$F$_2$.HCl.0.5 H$_2$O) C, H, N, Cl.

(R)-2β-Carbomethoxy-3β-diphenylmethoxytropane (R-11)

(R)-Ecgonine methyl ester, R-3, (0.5 mg, 2.5 mmol), benzhydrol (0.55 g, 3.0 mmol), p-toluenesulfonic acid monohydrate (0.72 mg, 3.6 mmol) and benzene (50 mL) in a 100 mL round bottom flask fitted with Dean-Stark trap and condenser were heated at reflux for 20 h. Benzene was removed in vacuo. The residue was chromatographed with silica gel (10% Et$_3$N in hexane, 10% Et$_3$N in Et$_2$O) to afford (R)-2β-carbomethoxy-3β-(diphenylmethoxy)tropane, R-11, (0.22 g, 24%) as a white solid after recrystalized from hexane: mp 94°–95° C.; R$_f$ 0.63 (5% MeOH/EtOAc+ NH4OH); Anal. (C$_{23}$H$_{27}$NO$_3$) C, H, N.

(R)-(–)-2β-Carbomethoxy-3α-diphenylmethoxytropane (R-12)

(R)-Alloecgonine methyl ester, R-6, (0.75 mg, 3.76 mmol), benzhydrol (1.04 g, 5.65 mmol), p-toluenesulfonic acid monohydrate (867 mg, 4.5 mmol) and benzene (50 mL) in a 100 mL round bottom flask fitted with Dean-Stark trap and condenser were heated at reflux for 4 h. Benzhydrol (500 mg) was added and the reaction mixture was heated at reflux for another 16 h. Benzene was removed in vacuo. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed over silica gel (3% NH$_4$OH, 2% MeOH in EtOAc) to afford (R)-2β-carbomethoxy-3α-diphenylmethoxytropane, R-12, (0.77 g, 81%) as a pale yellow viscous oil: R$_f$ 0.65 (5% MeOH/EtOAc+NH$_4$OH); HCl salt: mp 181°–182° C. Anal. (C$_{23}$H$_{27}$NO$_3$.HCl) C, H, N, Cl.

(S)-(+)-2β-Carbomethoxy-3α-diphenylmethoxytropane (S-12)

(S)-Alloecgonine methyl ester (193 mg, 0.97 mmol), benzhydrol (386 mg, 2.09 mmol), p-toluenesulfonic acid monohydrate (288 mg, 1.5 mmol) and benzene (50 mL) in a 100 mL round bottom flask fitted with Dean-Stark trap and condenser was heated at reflux for 18h. Benzhydrol (200 mg) and p-toluenenesulfonic acid monohydrate (70 mg) were added and the reaction mixture was heated for another 5 h. Benzene was removed. The residue was dissolved in water (10 mL), basified with NH$_4$OH and extracted with CH$_2$Cl$_2$ (2×50 mL). The dried (K$_2$CO$_3$) extracts were concentrated to dryness. The residue was chromatographed with silica gel (2% NH$_4$OH, 3% MeOH in EtOAc) to afford (S)-(+)-2β-carbomethoxy-3α-diphenylmethoxytropane (271 mg, 77%) as a yellow viscous oil: R$_f$ 0.65 (5% MeOH/EtOAc+NH$_4$OH)$_;$. HCl salt mp 178°–179° C. Anal. (C$_{23}$H$_{27}$NO$_3$.HCl) C, H, N.

(S)-(+)-2β-Carbomethoxy-3α-(di-4-chlorophenyl-methoxy)tropane (S-13)

(S)-Alloecgonine methyl ester (180 mg, 0.9 mmol), 4,4'-dichlorobenzhydrol (460 mg, 1.8 mmol), p-toluenesulfonic acid monohydrate (288 mg, 1.5 mmol) and benzene (50 mL) in a 100 mL round bottom flask fitted with Dean-Stark trap and condenser was heated at reflux for 18h. 4,4'-dichlorobenzhydrol (230 mg) and p-toluenenesulfonic acid monohydrate (50 mg) were added and the reaction mixture was heated for another 5 h. Benzene was removed The residue was dissolved in water (10 mL), basified with $NH_4OH$ and extracted with $CH_2Cl_2$ (2×50mL). The dried ($K_2CO_3$) extracts were concentrated to dryness. The residue was chromatographed over silica gel (2% $NH_4OH$, 2% MeOH in EtOAc) to afford (S)-(+)-2β-carbomethoxy-3α-(di-4-chlorophenylmethoxy)tropane (226 mg, 58%) as a off-white crystalline solid: mp 115°–117° C.; $R_f$ 0.53 (10% $Et_3N$/ether); [Anal. ($C_{23}H_{25}NO_3Cl_2$) C, H, N.

(S)-(+)-2β-Carbomethoxy-3α-(di-4-methylphenyl-methoxy)tropane (S-14)

(S)-Alloecgonine methyl ester (200 mg, 1.0 mmol), 4,4'-dimethylbenzhydrol (426 mg, 2.0 mmol), p-toluenesulfonic acid monohydrate (288 mg, 1.5 mmol) and benzene (50 mL) in a 100 mL round bottom flask fitted with Dean-Stark trap and condenser was heated at reflux for 18h. 4,4'-Dimethylbenzhydrol (200 mg) and p-toluenenesulfonic acid monohydrate (50 mg) were added and the reaction mixture was heated for another 5 h. Benzene was removed. The residue was dissolved in water (10 mL), basified with $NH_4OH$ and extracted with $CH_2Cl_2$ (2×50 mL). The dried ($K_2CO_3$) extracts were concentrated to dryness. The residue was chromatographed with silica gel (2% $NH_4OH$, 3% MeOH in EtOAc) to afford (S)-(+)-2b-carbomethoxy-3a-(di-4-methylphenylmethoxy)tropane (316 mg, 80%) as a yellow viscous oil; $R_f$ 0.70 (5% MeOH/EtOAc+$NH_4OH$); HCl salt: mp 156°–157° C. Anal. ($C_{25}H_{31}NO_3$ .HCl) C, H, N, Cl.

(S)-(+)-2β-Carbomethoxy-3α-(9-fluorenoxy)tropane (S-15)

(S)-Alloecgonine methyl ester (200 mg, 1.0 mmol), 9-fluorenol (366 mg, 2.0 mmol), p-toluenesulfonic acid monohydrate (288 mg, 1.5 mmol) and benzene (50 mL) in a 100 mL round bottom flask fitted with Dean-Stark trap and condenser was heated at reflux for 18h. 9-Fluorenol (366 mg) and p-toluenenesulfonic acid monohydrate (80 mg) were added and the reaction mixture was heated for another 5 h. Benzene was removed. The residue was dissolved in water (10 mL), basified with $NH_4OH$ and extracted with $CH_2Cl_2$ (2×50 mL). The dried ($K_2CO_3$) extracts were concentrated to dryness. The residue was chromatographed with silica gel (2% $NH_4OH$, 5% MeOH in EtOAc) to afford (S)-(+)h2β-carbomethoxy-3α-(9-fluorenoxy)tropane (182 mg, 50%) as a yellow viscous oil; $R_f$ 0.62 (5% MeOH/EtOAc +$NH_4OH$); HCl salt: mp 153°–155° C. Anal. ($C_{23}H_{25}NO_3$. HCl. 0.5 $H_2O$) C, H, N, Cl.

Synthesis of 2β-Carbomethoxy-3β-diphenylmethoxytropanes (4a)

The β-analogs, 4'a–e, (FIG. 5A) are prepared by reaction of suitably substituted diphenyldiazomethane with ecgonine methyl ester, 11'. Ecgonine methyl ester (11') is prepared in quantitative yield from (–)-cocaine by sequential hydrolysis, dehydration with $POCl_3$, and Fischer esterification with MeOH as follows.

(–)-Cocaine (6.3 g, 0.02 mol) and 0.8N HCl (50 ml) are combined and heated at reflux overnight. The reaction mixture is cooled to room temperature and extracted with ether (25 ml). The aqueous layer is concentrated to dryness. $POCl_3$ (20 ml) is added to the residue and heated at reflux for 1 hour. Excess $POCl_3$ is removed under reduced pressure. After chilling the residue (dry ice acetone bath), MeOH (30 ml) is added. The mixture is warmed slowly to room temperature with swirling, and the MeOH is removed under reduced pressure. The residue is dissolved in water (50 ml), basified with $NH_4OH$, saturated with NaCl and extracted with ether (3×50ml). The combined ether extracts are dried over $K_2CO_3$, filtered and concentrated to dryness. The residue is purified by flash chromatography with 5% MeOH in EtOAc as eluent to afford 3.6 g (100%) of product as a light brown oil [$R_f$ 0.45 (10% MeOH in EtOAc+$NH_4OH$); $^1$H NMR (60 MHz, $CDCl_3$) δ1.4–2.2(m,6H), 2.35 (s,3H, $NCH_3$), 2.4+3.4(m,2H), 3.58(s, 3H, $OCH_3$), 6.83(m, 1H)].

Resolution is not required in this procedure since all stereochemistry is controlled by the starting material (–)-cocaine. Approximately 50 mg of Compounds 4'a–4'e are prepared by this route.

Synthesis of 2β-Carbomethoxy-3β phenyltropanes

To prepare the 2β-carbomethoxy-3β phenyltropanes, the general synthetic route illustrated in FIG. 12 is utilized. The essential feature of this synthetic route is the reaction of a suitable aromatic Grignard reagent (derived from haloaromatic compounds such as 17', 18' or 19') with anhydroecgonine methyl ester, (12'). The resultant mixture of isomers at C-2 are separated to obtain the pure 2β-carbomethoxy products. This work-up procedure improves considerably on the earlier published procedures of Clarke et al. (J. Med. Chem. 16:1260, 1973) and offers some advantage over the recently published procedure of Milius et al (J. Med. Chem. 34, 1728, 1991). (WIN35,428: β: 11%) and Carroll et al. (J. Med. Chem. 34:2719, 1991) (WIN 35,065-2: $R_1=R_2$=H: β:48%).

CFT (13'e) is prepared as follows. A mixture of 4-fluorophenylmagnesium bromide (2M, 5.5 ml, 11 mmol) and anhydrous ether (30 ml) was cooled to –20° C. Anhydroecgonine methyl ester (1.0g, 5.5mmol) in anhydrous ether (30ml) was added dropwise. The reaction mixture was stirred at –20° for 1 hr. Ethereal HCl (1.7M, 15 ml) was added, stirred for a few minutes and then ice (ca. 100 g) was added. The reaction mixture was allowed to warm to room temperature. The aqueous layer was extracted with $CH_2Cl_2$ (2×50ml). The $CH_2Cl_2$ layers were combined and washed with dilute $NH_4OH$, dried over $K_2CO_3$, filtered and concentrated to afford 300 mg of mainly the α-isomer. The aqueous layer, after $CH_2Cl_2$ extraction, was basified with $NH_4OH$, saturated with NaCl and extracted again with $CH_2Cl_2$ (3×50ml). The combined $CH_2Cl_2$ layers was dried over $K_2CO_3$, filtered and concentrated to afford 890 mg (58%) of the β-isomer. Further purification by preparative TLC (eluent: 3% $Et_3N$ in ether) provided CFT as a white solid (500 mg, 33%) [mp 91°–92° C.; $R_f$ 0.42(i-$PrNH_2$:$Et_2O$:pentane::5:30:65); $^1$H NMR (400 MHz, $CDCl_3$) δ1.57–1.75(m,3H), 2.0–2.2(m,2H), 2.23(s,3H, $NCH_3$), 2.56(ddd,1H,H-4), 2.86(m, 1H,H-2), 2.98(m, 1H,H-3), 3.36(m, 1H,H-5), 3.50(s,3H, $OCH_3$), 3.55(m,1H,H-1), 6.9–7.25(m,4H,ArH) ]. The α-epimer had mp 66°–67° C. [$R_f$ 0.35 (i-$PrNH_2$:$Et_2O$:pentane::5:30:65) $^1$H NMR (400 MHz, $CDCl_3$) 61.58–1.72(m,2H,H-6,7), 1.8–1.95(m,3H), 2.10(ddd, 1H,H-4), 2.40(s,3H,$NCH_3$), 30.5(m, 1H,H-2), 3.10(ddd,1H,H-3), 3.24(m, 1H,H-5), 3.40(m, 1H,H-1), 3.50(s,3H, $OCH_3$) , 6.9–7.25(m,4H,ArH)].

Routinely, total yields of about 80% (CFT: β: 60%; α: 20%) are obtained, and purification of the epimers is greatly facilitated by taking advantage of the relative pKa's of compounds such as 14' and 15'. Thus the Grignard reaction with 12' is carried out at −20° C. and quenched with ethereal HCl, and the α- and β-isomers (e.g., 14 and 15) are extracted separately with organic solvent at different pH's.

Using the same procedure, compounds 13'a–d are also prepared using suitable mono- and di-substituted haloaromatics as precursors for the required Grignard reagents.

Specifically, (−)-cocaine, 1', is treated with dilute HCl followed by dehydration with $POCl_3$ and subsequent reaction with MeOH, to provide R-(−)-anhydroecgonine methyl ester, 12'. This compound is then used in the subsequent Grignard reactions. Product 13a' is obtained directly upon purification of the isomeric mixture obtained from the reaction. In the case of the 3,4-dioxygenated moieties, prior protection is required before the Grignard reagent itself is prepared. For this purpose, an acetonide, 18', may be used since the deprotection of the acetonide product 14' can be carried out under mild conditions. No epimerization at C-2 occurs. In an alternative protection route, 3,4-dimethoxy bromobenzene (17'), is utilized as starting material for the Grignard reaction. The product, is then deprotected with $BBr_3$ to obtain the catechol 13b'. In either approach, compound 13d' is readily available by reaction of 13b' with acetic anhydride in pyridine.

It should be noted that the monomethoxy compound, 13':$R_1$=H,$R_2$=$OCH_3$, has been prepared, first by Clarke (1.2% yield) (J. Med. Chem. 16:1260, 1973), and then more recently by Carroll in 11% yield. (J. Med. Chem. 34:883, 1991).

Particular examples of 2β-carbomethoxy-3β phenyl tropane analogs according to the invention were synthesized as follows.

2β-Carbomethoxy-3β-(4-chlorophenyl)tropane. This compound was prepared as shown in FIG. 12. Yield was 15%. Quenching was performed as described by Clarke et al. (supra). The workup was as described above for CFT [mp 118°–119° C. (white solid); $R_f$ 0.49 (i-$PrNH_2$:$Et_2O$:pentane::3:30:67); $^1$H NMR (60 MHz, $CDCl_3$) δ1.4–2.1(m,6H), 2.25(s,3H,$NCH_3$), 2.25–3.1(m, 2H), 3.50(s,3H,$OCH_3$), 7.26(s,4H)].

2β-Carbomethoxy-3β- (3,4-dichlorophenyl)tropane. This compound was prepared as shown above for FIG. 12. Yield was 14%. Quenching was performed as described by Clarke et al. (supra). The workup was as described above for OFT [mp 82.5°–83.5° C. (white solid); $R_f$ 0.43 (i-$PrNH_2$:$Et_2O$:pentane::3:30:67); $^1$H NMR (400 MHz, $CDCl_3$) δ1.6–1.7(m,1H,H-2), 2.0–2.1(m,2H) , 2.21(s,3H, $NCH_3$), 2.50(ddd,1H,H-4) , 2.86(m, 1H,H-2) , 2.92(m, 1H,H-3), 3.33(m, 1H,H-5) , 3.52(s,3H, $OCH_3$), 3.55(m, 1H,H-1) , 7.07–7.32(m,4H,ArH)].

2β-Carbomethoxy-3β-(3-bromophenyl)tropane. This compound was prepared as shown in FIG. 12. Yield was 27% [$R_f$ 0.56 (i-$PrNH_2$:$Et_2O$:pentane: :5:30:65); $^1$H NMR (400 MHz, $CDCl_3$) δ1.56–1.71(m,3H), 2.07–2.2(m,2H, H-6, 7), 2.20(s,3H,$NCH_3$), 2.52(ddd,1H,H-4), 2.87(m,1H,H-2) , 2.94(m, 1H,H-3), 3.33(m, 1H,H-5), 3.52(s,3H, $OCH_3$) , 3.55(m, 1H,H-1), 7.1–7.4(m,4H,ArH)].

2β-Carbomethoxy-3β- (3-tributylstannylphenyl)tropane. 2β-Carbomethoxy-3β- (3-bromophenyl)tropane (0.9 g, 2.7 mmol) in toluene (16 ml) was degassed by bubbling nitrogen into the mixture. Bistributyltin (3.32 g, 6.25 mmol) was added, followed by tetrakis (triphenylphosphine) palladium (48.8 mg, 0.042 mmol). Degassing was continued for another 15 minutes.

The reaction mixture was heated at reflux for 2.5 hours, filtered through celite and washed with $CH_2Cl_2$. The filtrate was concentrated to dryness. The residue was purified by flash chromatography with 2% i-$PrNH_2$ (in hexane as eluent) to afford 690mg (47%) of a light brown oil [$R_f$ 0.73 (i-$PrNH_2$.$Et_2O$:hexane::3:30:67); $^1$H NMR (400 MHz, $CDCl_3$) δ0.8–1.5(m,27H), 1.5–1.76(m,3H) , 2.1–2.2(m,2H), 2.21(s,3H,$NCH_3$), 2.56(ddd,1H,H-4), 2.89(m,1H,H-2), 2.95(m,1H,H-3), 3.35(m,1H,H-5), 3.45(s,3H, $OCH_3$), 3.52(m,1H-H-1), 7.15–7.24(m,4H,ArH)].

2β-Carbomethoxy-3β-(3-iodophenyl)tropane. 2β-Carbomethoxy-3β-( 3-tributylstannylphenyl)tropane (155 mg, 0.28 mmol) in $CH_2Cl_2$ (20 ml, dried over molecular sieves) was degassed by bubbling nitrogen for 10 minutes. Iodine (427 mg, 1.7 mmol) was added, and the reaction mixture was stirred overnight at room temperature under nitrogen. The reaction mixture was quenched with 10 ml of 1% $Na_2S_2O_3$. The aqueous layer was extracted with $CH_2Cl_2$ (2×20ml). The combined $CH_2Cl_2$ layers were dried over $K_2CO_3$, filtered, and concentrated to dryness. The residue was triturated with a small amount of $CH_2Cl_2$, and the white insoluble material was filtered and stirred with $CH_2Cl_2$ and dilute $NH_4OH$ until dissolved. The $CH_2Cl_2$ layer was dried over $K_2CO_3$, filtered, and concentrated to afford 61 mg (56%) of product [(60 MHz, $CDCl_3$) δ1.22–2.11(m,4H), 2.22(s,3H,$NCH_3$), 2.45–3.5(m,2H), 3.53(s,3H, $OCH_3$), 6.85–7.65(m,4H,ArH)].

The 1,5-naphthalendisulfonate salt was prepared by adding 1,5-napthalenedisulfonic acid tetrahydrate (60 mg, 1.01 eq.) in reagent alcohol to the product. The salt was recrystallized from reagent alcohol and ether to afford 94 mg of product (82%). [$R_f$ 0.52 (i-$PrNH_2$:$Et_2O$:hexane::3:30:67); $^1$H NMR (400 MHz, $CDCl_3$) δ1.75–.1.79 (m, 1H), 1.98–2.25 (m, 4H), 2.48(ddd,1H,H-4), 2.67 (s,3H,$NHCH_3$), 2.95(dd,1H,H-2), 3.25(s,3H, $OCH_3$), 3.37 (m,1H,H-3), 3.80(m,1H,H-5), 3.93(m,1H,H-1), 6.97(t,1H,ArH), 7.09(m, 1H,ArH), 7.45(m,3H,ArH), 8.09(d,2H,ArH), 8.90(d,2H, ArH)].

2β-Carbomethoxy-3β- (4-fluorophenyl)nortropane. 2β-Carbomethoxy-3β- ( 4-fluorophenyl)tropane (70 mg, 0.25 mmol) and α-chloroethyl chloroformate (ACE-Cl) (0.3 ml, 2.9 mmol) were combined and heated at 100° C. (oil bath temperature) for 1 hour. Excess ACE-Cl was then removed under reduced pressure, and methanol (10 ml) was added to the residue. The mixture was then heated at reflux for 30 minutes and then concentrated to dryness. The residue obtained was dissolved in $CH_2Cl_2$ (25ml), washed with saturated $Na_2CO_3$ solution, dried over magnesium sulfate, filtered, and concentrated to afford the crude demethylated product (78 mg). Purification by preparative TLC (i-$PrNH_2$:EtOAc:hexane::3:47:50) gave the product as a tan solid [23 mg (35%): mp 110°–112° C.,$R_f$ 0.18 (i-$PrNH_2$:EtOAc:hexane:: 3:47:50); $^1$H NMR ($CDCl_3$) δ0.75–3.23(m,8H), 3.42(s,3H, $OCH_3$), 3.75(m,3H), 6.78–7.38(m,4H,ArH)].

2β-Carbomethoxy-3β- (4-chlorophenyl)nortropane. This compound was prepared as described below. Yield was 46% [Mp. 97°–98° C. (beige solid); $R_f$ 0.18 (i-$PrNH_2$:EtOAc:hexane::3:47:50); $^1$H NMR (60 MHz, $CDCl_3$) δ0.7–3.3(m,8H), 3.43(s,3H, $OCH_3$), 3.6(m,3H), 7.1–7.4(m,4H,ArH)].

2β-Carbomethoxy-3β-(3,4-dichlorophenyl)nortropane. This compound was prepared as described below. Yield was 65%. (Eluent for preparative TLC: 10% $Et_3N$ in ether) [Mp. 102°–103° C. (beige solid); $R_f$ 0.19 (10% $Et_3N$ in ether); $^1$H NMR (60 MHz, $CDCl_3$) δ0.87–3.4(m,8H), 3.48(s,3H, $OCH_3$), 3.8(m,3H), 7.0–7.53(m,4H,ArH)].

Certain of these analogs were characterized by elemental analysis. The results are shown in Table 1.

TABLE 1

Table of Elemental Analyses

| Compound | EXPERIMENTAL | | | | CALCULATED | | | |
|---|---|---|---|---|---|---|---|---|
| | C | H | N | Cl | C | H | N | Cl |
| 13'e | 69.35 | 7.29 | 5.01 | | 69.29 | 7.27 | 5.05 | |
| 13' ($R_1$ = N, $R_2$ = Cl) | 65.31 | 6.82 | 4.77 | 12.06 | 65.41 | 6.68 | 4.77 | 12.07 |
| 13'a | 58.46 | 5.87 | 4.24 | 21.50 | 58.55 | 5.83 | 4.27 | 21.60 |
| 13' ($R_1$ = SnBu$_3$, $R_2$ = H) | 61.38 | 8.61 | 2.50 | | 61.32 | 8.64 | 2.55 | |
| 13' ($R_1$ = I, $R_2$ = H)* | 42.85 | 4.70 | 1.93 | | 42.92 | 4.71 | 1.93 | |
| nor 13'e | | 68.17 | 6.96 | 5.15 | | 68.42 | 6.89 | 5.32 |
| nor 13' ($R_1$ = H, $R_2$ = Cl)** | 63.26 | 6.37 | 4.92 | 12.52 | 63.68 | 6.56 | 4.93 | 12.47 |
| nor 13'a | | 57.45 | 5.42 | 4.49 | 22.63 | 57.34 | 5.46 | 4.4622.57 |

*Napthalene disulfonate salt trihydrate, Experimental: S-8.89, I-17.38, Calculated: S-8.81, I-17.44
**As a 0.25 hydrate

Syntheses of Other Phenyl Tropanes

Other phenyl tropanes of the invention are synthesized as follows.

To provide the nor compounds, any of the N-methyl compounds 3', 4' or 13' is dealkylated by treatment with a chloroformate such as vinyloxychloroformate (VOC-chloride) or α-chloroethyl chloroformate, (ACE-chloride) and hydrolyzed. Introduction of the alkyl groups at nitrogen is then carried out by reaction of the nor compounds with the relevant alkyl halides in a solvent such as DMF in the presence of a base such as potassium carbonate. In this manner, the N-substituted benztropines, e.g., [2β-carbomethoxy-3(α or β)-benztropine] and CFT and analogs (2β-carbomethoxy-3β-phenyl tropanes) are prepared.

The 2β-ketones are prepared from compounds 3", 4" and 13" by reaction with a suitably chosen alkyl lithium reagent, such as methyl, ethyl, propyl, phenethyl, or phenalkyl lithium.

Synthesis of Cocaine Analogs Lacking a Ring Nitrogen

To prepare the CFT and benztropine analogs of the invention which lack a ring nitrogen, the following procedures may be utilized.

Synthesis of 2β-Carboxymethyl-3β-arylbicyclo[3.2.1]octanes. To prepare the oxa, thia, and carbo analogs of CFT, the synthetic procedure shown for an oxabicyclo system in FIG. 13 is followed. The essential feature of this synthesis is the reaction of a suitable aromatic Grignard reagent with the oxabicyclo[$3.2.1$]octene methyl ester 24'. This methyl ester is obtained by dehydration of the 3-hydroxy compound, 23', which is in turn, obtained by reduction of the ketone, 22' with sodium borohydride. The ketone 22' is prepared as described by Brownridge and Chan (Tetrahedron Letters, 46:4437, 1979). Resolution is carried out on the alcohol, 23' (or 27'), by crystallization of a chiral ester. Thus, 2,5-dimethozytetrahydrofuran, 20' (the appropriate thia or carbon analogs are used as precursors for the synthesis of the thia and carbbicyclo[$3.2.1$]octanes) is reacted with 1,3-bis(t-rimethylsiloxy)- 1-methoxybuta-1,3-diene, 21', in methylene chloride in the presence of titanium tetrachloride to give 22' in 79% yield Reduction of the ketone, 22', with sodium borohydride then provides the alcohol as a mixture of stereoisomers, with 23' as a major stereoisomer present and 27' as the minor. The desired syn stereoisomer is separated and the enantiomers are separated by fractional crystallization of chiral esters such as the tartrate ester. The enantiomerically pure alcohol is dehydrated and reesterified with phosphorus exychloride and methanol to provide the anhydromethyl ester, 24' which is reacted with a suitably chosen Grignard reagent (described above) to provide the desired products, (for example, 25').

Synthesis of 2β-Carboxymethyl-3α-diphenylmethoxy [$3.2.1$]octanes. To prepare the oxa analogs of the 3α-diphenylmethoxytropanes, the synthetic procedure shown in FIG. 13 is followed. The 3α-diphenylmethoxy[$3.2.1$]octanes are made from the ketone 22'. Either reduction of 22' with sodium borohydride will provide 27' as the minor isomer, or reduction with sodium will provide 27'. As before, 27' is then reacted with a suitably chosen diphenyl diazomethane to provide the desired compounds, 28'.

Synthesis of 2β-Carboxymethyl-3β-diphenylmethoxy [3.2.1]octanes. To prepare the oxa analogs of the 3β-diphenylmethoxytropanes, the synthetic procedure shown in FIG. 9 is followed. Compound 23' is prepared as described above resolved, and purified, and the enantiomerically pure alcohol, 23', is then reacted with a suitably selected diphenyldiazomethane to provide the desired target compounds, 26'.

Reaction of 25', 26' or 28' with suitably chosen lithium reagents will provide the 2β-ketones, as described above.

Compound Characterization

All target compounds are prepared as the free bases or salts, e.g., the naphthalene-1,5-disulfonate, tartrate, or hydrochloride salts. Characterization of the compounds is carried out using standard methods of high field NMR spectra as well as IR, MS and optical rotation. Elemental analysis, TLC and/or HPLC is used as a measure of purity. A purity of >98% is preferred before biological evaluation of these compounds is undertaken. These standards have been easily achieved in prior preparations of CFT itself as well as in the preparation of a number of CFT analogs.

IV. Binding Assays for Candidate Compounds

To evaluate derivatives as to selectivity for the dopamine transporter, compounds are screened in radioreceptor assays using both [$^3$H]CFT and [$^3$H]citalopram as probes for the dopamine and serotonin receptors, respectively. The relative affinities of a compound for either site establishes whether it binds selectively to the dopamine transporter or non-selectively to the serotonin transporter as well. Assays are carried out as follows.

Competition studies to determine the potency of a compound for inhibiting specifically bound [$^3$H]CFT in monkey caudate-putamen membranes are conducted using 0.3–10nM [$^3$H]CFT and the brain tissue of drug- and disease-free cynomolgus monkeys (Macaca fascicularis), which is stored at −85° C. The caudate-putamen is dissected from coronal sections and suspended in 10 vol Tris-HCl (50 mH, pH 7.4 at 4° C.). The tissue is homogenized in a Potter-Elvehjem (glass-teflon) homogenizer with 8 up-and-down strokes using a Tri-R electronic control stirrer motor (2000 rpm approx.). The homogenate is centrifuged twice for 30 min at 38,000×g and resuspended in buffer to yield a final concentration of 4 mg original wet tissue weight/ml of assay buffer. The assay medium contains, in order of addition, buffer (50 mM, Tris-HCl, 120mM NaCl) or buffer plus test compound (0.2 ml); [$^3$H]CFT (80 Ci/mMol, 0.2 ml, 10 nM); and membrane suspension (0.2 ml) to a final volume of 0.6 ml. Unlabeled (–)-cocaine (30 μM) serves as the baseline drug to detect non-specific. binding. Incubation proceeds at 4° C. for 60 min, and the assay is terminated by vacuum filtration over glass fiber filters (Whatman GF/B) pre-soaked with 0.1% bovine serum albumin. The filters are washed with two 5-ml rinses of ice-cold buffer, incubated overnight in fluor (Beckman ready-solve, EP grade), and total radioactivity determined by liquid scintillation spectrometry at 50% counting efficiency. All assays are performed in triplicate, and each experiment is repeated at least twice using tissue from different brains.

To assay binding of the analog to the serotonin transporter, analogs are tested for their ability to compete with labeled [$^3$H]citalopram, a high affinity and selective ligand for serotonin transporter sites (D'Amato et al., J. Pharmacol. Exp. Ther. 242:364–371, 1987). Radioreceptor assays are conducted using tissues prepared as described above. Analogs are incubated with buffer (50 mM Tris HCl; 100mM NaCl), [$^3$H]citalopram (1 nM), and tissue (1 mg/ml wet tissue weight), incubated 2 h at 4° C., and the incubation terminated by rapid filtration. Non-specific binding is monitored with fluoxetine (1 μM). The sites may first be characterized using other serotonin uptake inhibitors (sertraline, citalopram, fluoxetine, paroxetine, imipramine), other monoamine uptake inhibitors (cocaine, mazindol, GBR 12909, talsupram), and neurotransmitters (dopamine, serotonin, norepinephrine). Subsequently, the potency of CFT or the analog is determined. Parallel studies are conducted with [$^3$H]CFT in order to determine the relative potencies of the analogs at each transporter.

Using such an approach, several of the analogs described herein were tested for their ability to inhibit the binding of [$^3$H]CFT to primate caudate-putamen; results are presented in Table 2. Inhibition by (–)-cocaine and CFT (4a) are presented as reference points.

TABLE 2

| Compound | $R_1$ | $R_2$ | IC$_{50}$ (nM) |
| --- | --- | --- | --- |
| 4'a (CFT) | H | F | 11.0 ± 1 |
| 4'b (CCT) | H | Cl | 1.40 ± 0.035 |
| 4'c (CDCT) | Cl | Cl | 1.09 ± 0.015 |
| 4'd (3-CBT) | Br | H | 7.93 ± 0.077 |
| 4'e (3-CIT) | I | H | 27.8 ± 3.05 |
| 4'f | Sn(C$_4$H$_9$)3 | H | 1080 ± 165 |
| 4'g (WIN 35, 065-2) | H | H | 65 ± 12 |
| 4'h (RTI-55) | H | I | 1.08 ± 0.06 |
| (–)-cocaine | | | 95.6 ± 14.4 |

V. Behavioral Effects of Candidate Compounds

To the degree possible, candidate compounds for molecular probes should have a full range of cocaine-like biological activity. Candidate compounds found above to have cocaine-like properties in binding studies are assessed further for cocaine-like discriminative stimulus (subjective) effects and their capacity to maintain intravenous self-administration.

For drug discrimination and self administration studies, experiments are conducted with rodents or squirrel monkeys (*Saimiri sciureus*) seated in standard primate chairs enclosed in ventilated, sound-attenuating chambers. The chairs are equipped with response levers, stimulus lights, food pellet dispensers, and pumps for injecting drugs intravenously. Four animals are studied in each experiment, with each subject receiving all drug treatments whenever possible. Response rates and temporal patterns of responding are monitored continuously during daily experimental sessions. Effects of drugs are analyzed in individual subjects by comparing performances during drug sessions with those during control sessions. In experiments involving drug self-administration, i.v. injections of drug solutions (0.2 ml, infused over 200 msec) are scheduled intermittently (as described below). Monkeys in these studies are prepared with indwelling venous catheters according to the general procedures described by Herd et al., (Am. J. Physiol. 27:24–29, 1969). Surgery is conducted in aseptic conditions under halothane/oxygen anesthesia. Catheters are passed by way of a jugular or femoral vein to the level of the right atrium. The distal end of the catheters is passed subcutaneously to a midscapular exit point. Catheters are flushed with 0.9% saline solution and sealed with stainless steel obturators when not in use. Monkeys wear nylon mesh jackets at all times to protect the catheters.

VI. DRUG DISCRIMINATION

Drug discrimination experiments are conducted using cumulative-dose procedures similar to those described in Madras et al. (Soc. Neurosci. Abst. 16:14, 1990; Pharmacol. Biochem. Behav. 35:949–953, 1990) and Spealman et al. (J. Pharmacol. Exp. Ther. 258:945–953, 1991). Drugs acting in the central nervous system can induce changes in interoceptive states that serve as discriminative stimuli in animals, and there is high pharmacological specificity in the classification of drugs based on their generalized discriminative-stimulus effects. Cumulative-dose procedures have a major advantage over single-dose procedures in that they permit determination of a full dose-effect curve during a single experimental session. Preliminary experiments are first conducted to determine the effective dose ranges and the onsets and durations of action of the drugs. Good agreement has been found between the effects of drugs determined by cumulative-dose procedures and by single-dose procedures when appropriate parameters are selected. Effective doses are studied using single-dose procedures to directly assess the comparability of effects determined by the two techniques.

Drug-discrimination assays are used to characterize the effects of drugs in monkeys trained to discriminate cocaine from vehicle. During experimental sessions, monkeys are seated in chairs equipped with two levers, and a food pellet dispenser mounted between the levers. Each monkey is trained under a 10-response fixed-rate (FR) schedule of food presentation to respond differentially on the left and right levers depending on whether cocaine or vehicle is injected. After i.m. injection of cocaine, 10 consecutive responses on one lever (left for half the monkeys in each group, right for the reminder) will produce food; after i.m. injection of vehicle, 10 consecutive responses on the other lever will produce food. Responses on the inappropriate lever resets the FR requirement. Daily sessions consist of a variable number (n=1-4) of components of the FR schedule. Each component ends after the completion of 10 FRs or after 10 min, whichever occurs first, and each is preceded by an extended timeout period. During most sessions, vehicle is injected during the timeout period preceding the first n-1 components; drug is injected during the timeout period preceding the nth component of the session. During some sessions, however, vehicle is injected during all timeout periods to prevent an invariant association between the fourth component and injection of drug. The number of components per session is varied randomly from day to day. Training continues until a criterion of >90% of responses are made on the injection-appropriate lever. The training dose of cocaine is 0.3–1.0 mg/kg, depending on the performance of individual subjects.

Drug testing begins after criterion-level performances are maintained consistently. Thereafter, test sessions are conducted once per week, always preceded by training sessions with criterion performances. Test sessions consist of four FR components, with each component preceded by an extended timeout period. In each FR component, every tenth response, regardless of lever, produces food. Drugs are studied using the cumulative dosing procedure described previously. Incremental doses are injected i.m. during the timeout periods preceding sequential components of the FR schedule, permitting determination of a four-point dose-effect curve in a single session. In most experiments, five or six different doses of a test drug are studied by determining the effects of overlapping ranges of doses in separate sessions. A test drug is considered to substitute full for cocaine if it engenders >90% of responses on the drug-associated lever.

VII. DRUG SELF-ADMINISTRATION

Self-administration of cocaine and other psychomotor-stimulant drugs is studied under second-order schedules of i.v. drug injection (Bergman et al., J. Pharmacol. Exp. The. 251:150–155, 1989, Spealman et al., Pharmacol. Biochem. Behav. 31:1011–1013, 1991). Under these schedules, high rates of responding can be maintained for extended periods of time by only one or a few injections of drug per session. This feature is particularly useful for comparing drugs with different time courses, which may complicate interpretation of results if injections are scheduled more frequently. Squirrel monkeys are implanted with venous catheters as described previously and trained to respond under a second-order schedule of i.v. cocaine injection similar to the schedule described by Bergman et al. (1989, supra). In the presence of a red light, every 30th response (FR unit) produces a 1-sec change in illumination from red to amber (brief stimulus), and the first FR unit completed after elapse of a 10-min fixed-interval (FI) produces both the brief stimulus and an i.v. injection of cocaine. Following a timeout period, the entire cycle is repeated for a total of ten injections of drug per session.

Initially, responding is maintained using an injection dose of 100 μg/kg cocaine, which usually is optimal for developing i.v. self-administration. After consistent rates and patterns of responding are maintained by cocaine, the effects of a full range of doses of cocaine and of selected candidate drugs is determined. Drugs are studied in different order in different subjects, and experiments with one drug are completed before another drug is studied. Each dose is studied for a block of at least 5 sessions and until no systematic trends in responding are observed for at least 3 consecutive sessions. Blocks of sessions in which vehicle is substituted for drug and responding is extinguished separates experiments with different drugs.

VIII. PET IMAGING

A. PET Imaging Probes

The cocaine analogs described herein provide useful PET imaging probes. PET imaging has at least two applications: to evaluate the time course of accumulation of a candidate cocaine substitute in the brain as well as the duration of receptor occupancy and to monitor cocaine receptors and dopamine nerve terminals in competitor studies (see above).

Cocaine analogs of high affinity are most useful as PET imaging probes because the dose of radioactivity needed to image a target decreases along with decreases in organ dosimetry. In addition, CFT displays a markedly low level of non-specific binding. High affinity analogs are also preferable because dopamine may compete effectively with trace doses of low affinity analogs in vivo, thereby reducing the apparent accumulation in striatum. Affinity of a compound is determined using the in vitro binding assay, and distribution is determined by in vivo and ex vivo receptor autoradiography (described above).

Compounds may also be analyzed for possible in vivo breakdown. Arterial blood samples are withdrawn at predetermined intervals, plasma separated by centrifugation, basified, extracted with $CH_2Cl_2$, the solvent evaporated, and compound metabolites analyzed by HPLC. The percent of water soluble metabolites in the plasma residue is determined by radioactive monitoring and analyzed by HPLC. After appropriate corrections for decay, sensitivity, uniformity and attenuation, the collected image data is reconstructed for tissue concentration maps using a Hanning windowed filtered backprojection. The tissue concentration maps are combined with arterial plasma data to calculate receptor uptake using the model developed by Patlak et al., (Blood Flow Metab. 5:584, 1986). This model relies on the hypotheses (1) that the specific binding of [$^{11}$C]radioligand to striatal membranes can be considered as irreversible for the duration of the PET study; and (2) that non-specific ligand binding is distributed evenly through brain and can be determined from the activity in the cerebellum.

Arterial blood sampling of the monkey will be taken for the same period of time to determine the arterial blood activity curve. The brain distribution, striatum:cerebellar ratio as a function of time and the blood levels of the compound are performed in three monkeys. The following steps are used to evaluate model parameters. 1) Time course of plasma radioactivity is determined. 2) Plasma curves are corrected for metabolism of the tracer and a biexponential function (Gauss-Newton algorithm/non-linear curve-fitting) is fit to the data. 3) From dynamic PET images, time activity curves for striatum, occipital cortex and cerebellum are obtained. 4) The plasma activity of the tracer at the time of PET measurements is determined. 5) The corrected plasma curve at the time of the PET measurements is integrated. 6) The tissue activity ratio (t) [Striatum/Cerebellum]=f[integrated plasma activity (t)/plasma activity (t)] is determined. Initially striatum:cerebellar ratios are calculated as a function of time. The compounds with the highest striatal concentration, fastest blood clearance, least metabolism and least non-specific binding are most preferable in the invention.

Compounds to be used as imaging probes are labelled as follows. In the first step of the procedure, the salt form of the compounds is neutralized to the free amine. This procedure is performed each time before the labeling procedure is done. [$^{11}$C]methyl iodine is prepared as follows: nitrogen gas is bombarded for 15 minutes with 50 μA. The process of converting gaseous COffi to methyl iodine is automated and uses between 1.32–1.5Ci $^{11}CO_2$. A freshly prepared (under argon) LAH solution is used for the reduction of the $CO_2$. The methyl iodine specific activity is generally 1.32–1.5 Ci. The amine precursor is methylated with [$^{11}$C]methyl iodine in DMF. The mixture is heated at 80° C. for a period of 5 min. The mixture is then flushed with helium or argon into an HPLC system for separation and analysis. The specific activity of the final product should be between 1.–2. Ci/mmol. The column for separation of precursor-product is an Altech C18 prep-column. The solvent system is 40% acetonitrile, 60% water and 1% ammonia formate. The extract is evaporated and prepared for i.v. administration.

Prior to PET imaging studies, test animals are subjected to one magnetic resonance imaging (MRI) to determine stereotaxic coordinates of regions of interest using a stereotaxic head holder designed for these studies. The anaesthetized animal (ketamine 10–20 mg/kg/; xylazine 1–2 mg/kg) is placed on the computer controlled imaging table face down. The head is placed into a stereotaxic head holder and the table is moved until the plane of interest is positioned in the imaging field. Two planes of interest are selected, the caudate-putamen and the cerebellum and the selected brain levels are imaged sequentially. Generally, the compound (for example, [$^{11}$C]CFT (400–2,000 Ci/mmol; approximately 1–5 nmoles) is administered to control monkeys and the regional brain distribution association and dissociation rates determined. Following rapid intravenous injection of the compound, dynamic imaging in the selected brain level is started; 30 s scans for 5 min, 1 min scans for next 10 min, 2 min scans for 45 min and 5 min scans thereafter for 30 min. Arterial blood samples of 0.25–0.5 ml for determination of radioactivity and 1.2 ml (*) for determination of lipophilic metabolites by H.P.L.C. are collected according the following time table; 0, 15"30", 45", 60" (*), 75", 90", 105", 120"-(*),5'(*), 10'(*), 15', 20', 30'(*), 45', 60'(*), 75', 90'(*). Plasma and total blood radioactivity are counted in a well counter that is cross calibrated with the tomograph.

PET imaging may be carried but using any appropriate apparatus but is preferably carried out using coded single ring positron tomograph (Brownell et al., Intl. J. Imaging Syst. Tech. 1:207–217, 1989). The analog ring design offers a number of advantages for positron tomography. First, high resolution tomographs can be obtained without sacrificing sensitivity. The analog ring design does not use absorbing masks or intercrystal shielding and is not limited by rejecting photons scattered into adjacent detector elements. Second, high resolution can be obtained without mechanical motion. This results from the use of thin, closely packed detector elements and permits fast dynamic imaging in an easily assembled system (Burnham et al., IEEE Trans. Nucl. Sci. NS 32:889–893, 1991). A single ring analog coded position tomograph (PCR-I) may be used. PCR-I provides adequate resolution (spatial resolution of 4.5 mm) and sensitivity (46 kHz for the slice thickness of 1 cm and activity concentration of 1 μCi/ml) for quantitative biological studies. A moving computer controlled table connected to the camera enables imaging of sequential slices, so images can be acquired in three dimensions. Based on PCR-I, an analog coded cylindrical tomograph, PCR-II, capable of volumetric reconstruction of three-dimensional sources at 3 mm resolution has been designed (Brownell et al., Intl. J. Imaging Syst. Tech. 1:207–217, 1989) and may be used for further analysis.

PET imaging is carried out on conscious human subjects using the techniques outlined above or any other equivalent techniques. SPECT imaging may also be used on human subjects (see, e.g., Medicine, Scientific American, Inc., ed. Rubenstein and Federman, 1988; Jaszczak and Coleman, Invest. Radiol. 20:897, 1985; Coleman et al., Invest. Radiol. 21:1, 1986); preferably SPECT imaging employes gamma-imitting derivatives of the analogs described herein (e.g., analogs labelled with $^{123}$I or $^{99}$Tc).

XI. ANALYTICAL CONSIDERATIONS

All target compounds are prepared either as free bases or as suitable pharmacologically active salts such as hydrochloride, tartrate, naphthalene-1,5-disulfonate salts or the like. All target compounds are characterized and their purity analyzed prior to any biological evaluation. High field NMR spectra are measured as well as IR, MS and optical rotation for all test compounds. Elemental analysis, TLC and/or HPLC are used as a measure of purity. A purity of 98% is required before any biological evaluation of these compounds is undertaken.

X. THERAPY

The cocaine analogs described herein are useful as cocaine substitutes for treatment of cocaine addiction. The cocaine analogs, particularly the benztropine series, may also be useful for the treatment of neurodegenerative diseases, such as Parkinson's disease. For either application, the analogs may be administered, e.g., orally or intravenously in an appropriate dosage, generally 0.01–10 mg/kg.

TABLE 3

Analytical data

| COM-POUND | | ANALYTICAL DATA | | | | | | | |
|---|---|---|---|---|---|---|---|---|---|
| | | FOUND | | | | CALCULATED | | | |
| | | C | H | N | Cl | C | H | N | Cl |
| R-7 | (a) | 62.89 | 6.08 | 3.14 | 8.24 | 63.08 | 5.99 | 3.20 | 8.1 |
| R-8 | | 68.62 | 6.23 | 3.45 | | 68.81 | 6.28 | 3.49 | |
| R-9 | (b) | 59.29 | 6.39 | 2.97 | 7.64 | 59.41 | 6.29 | 3.01 | 7.62 |
| R-10 | (c) | 60.85 | 6.08 | 3.14 | 7.84 | 60.58 | 6.19 | 3.07 | 7.78 |
| S-7 | (d) | 62.63 | 6.02 | 3.14 | 8.07 | 62.53 | 6.02 | 3.17 | 8.02 |
| S-8 | | 68.92 | 6.31 | 3.47 | | 68.81 | 6.28 | 3.49 | |
| S-9 | | 68.57 | 6.3 | 3.47 | | 68.81 | 6.28 | 3.49 | |
| S-10 | (e) | 61.86 | 6.16 | 3.17 | 8.01 | 61.81 | 6.09 | 3.13 | 7.93 |
| R-11 | | 75.49 | 7.49 | 3.77 | | 75.59 | 7.45 | 3.83 | |
| R-12 | (a) | 68.62 | 7.06 | 3.48 | 8.92 | 68.73 | 7.02 | 3.49 | 8.82 |
| S-12 | (a) | 68.79 | 7.05 | 3.53 | 8.91 | 68.73 | 7.02 | 3.49 | 8.82 |
| S-13 | | 63.52 | 5.81 | 3.16 | 16.39 | 63.60 | 5.80 | 3.23 | 16.32 |
| S-14 | (a) | 69.71 | 7.59 | 3.18 | 8.33 | 69.83 | 7.50 | 3.26 | 8.24 |
| S-15 | (e) | 67.64 | 6.7 | 3.7 | 3.29 | 67.55 | 6.65 | 3.42 | 8.67 |

(a) HCl salt
(b) HCl. 1.5 H2O
(c) HCl. H2O
(d) HCl 0.2 H2O
(e) HCl 0.5 H2O

What is claimed is:

1. A compound of formula:

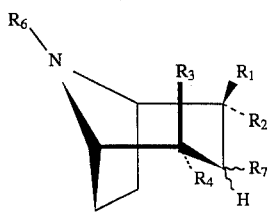

wherein the following conditions are imposed on that formula:
A. $R_7$ is s-linked, it being understood that the —H at position 3 has a linkage opposite to $R_7$;
B. $R_1$ and $R_2$ are —H,
C. one of $R_3$ and $R_4$ is —CO—$R_5$, where $R_5$ is —CH$_3$, CH$_2$CH$_3$, —(CH$_2$)$_n$CH$_3$, $(CH_2)_n$—Z, —Z, —O—CH$_3$, —O—CH$_2$CH$_3$, —O—Z, —O—CH(CH₃)₂, or —CH=CH₂, and the other of R₃ and R₄ is —H, where Z is C₆H₃XY, and X and Y are independently selected from the group consisting of: —H, —Br, —Cl, —I, —F, —OH, OCH₃, —CF₃, —NO₂, —NH₂, —CN, —NH—CO—CH₃, —N(CH₃)₂, —(CH₂)ₙCH₃, —CO—CH₃, and —C(CH₃)₃; and n=0–6;

D. R₆ is —H, —CH₃, CH₃CH₂—, CH₃(CH₂)ₙ—, —CH₂CHCH₂, —CH₂c(C₄H₇), —CH₂c(C₃H₅), —CH₂CF₃, —CH(CH₃)2, —CH₂CH₂OH, —CH₂(CH)ₙOZ', —2—(1-piperidinyl)ethyl, —2—(4-morpholinyl)ethyl, —(CH₂)ₙC₆H₅, —(CH₂)ₙC₆H₄X, —CH₂COCH₃, or XCH=CHCH₂—, where n and X are as defined above, and Z' is —H or a straight chain alkyl group of between 1 and 4 carbons;

E. R₇ is

1.
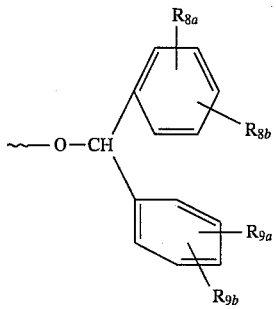

or

2.
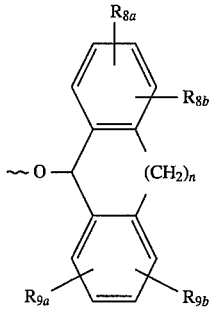

or

3.
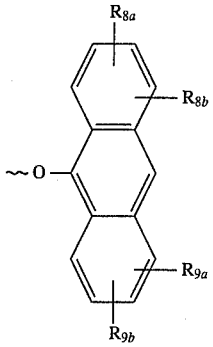

where R$_{8a}$, R$_{8b}$, R$_{9a}$, and R$_{9b}$ are independently selected from the group consisting of: —H, —Br, —F, —Cl, —I, —OH, —COCH₃, —OCH₃.

2. The compound of claim 1 wherein R₃ is —CO—R5.

3. The compound of claim 2 wherein R₁, R₂, and R₄ are —H.

4. The compound of claim 2 wherein R₆ is —CH₃ or I—CH=CH—CH₂—.

5. The compound of claim 1 wherein R$_{8b}$ and R$_{9b}$ are each —H, and R$_{8a}$ and R$_{9a}$ are substituents at the 4 position.

6. The compound of claim 1, wherein none of R$_{8a}$, R$_{8b}$, R$_{9a}$, and R$_{9b}$ are —H, and both of the pairs R$_{8a}$/R$_{8b}$ and R$_{9a}$/R$_{9b}$ are in the ¾ positions.

7. The compound of claim 1 wherein the pair R$_{8a}$ and R$_{8b}$ and the pair R$_{9a}$ and R$_{9b}$, are independently selected from —H and 2-, 3-, or 4-F; —H and 2-, 3- or 4-Cl; —H and 2-, 3-, or 4-I; 3,4-diCl; —H and 4-I; —H and —H; 3,4-diOH, 3,4-diOAc, 3,4-diOCH₃; 3 —OH and 4-Cl or 4-F; and 3-Cl or 3-F and 4 —OH.

8. The compound of claim 1 wherein R$_{8a}$/R$_{8b}$ and R$_{9a}$/R$_{9b}$ are both —H/4-F; —H/4-Cl; 3,4-diCl, —H/4-I, or —H/—H; or R$_{8a}$/R$_{8b}$ is —H/—H and R$_{9a}$/R$_{9b}$ is —H/4-F, —H/4-Cl, —H/4-I, or 3,4-diCl.

9. A compound of the formula:

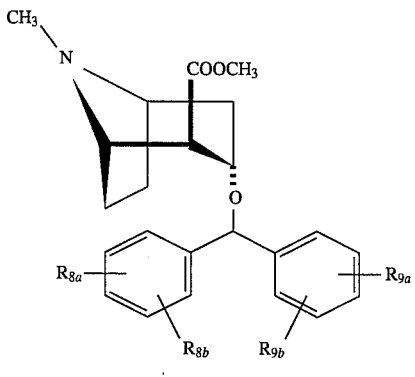

wherein R$_{8a}$, R$_{8b}$, R$_{9a}$, and R$_{9b}$ are independently selected from the group consisting of: —H, —Br, —F, —Cl, —I, —OH, —COCH₃, and —OCH₃.

10. The compound of claim 9 wherein R$_{8a}$ is —F.

11. The compound of claim 9 or 10 wherein R$_{8b}$ is —H.

12. The compound of claim 10 wherein R$_{8a}$ is at the 4 position.

13. The compound of claim 12 wherein said compound is (S)-(+)-2β-carbomethoxy-3α-(di-4-fluorophenylmethoxy)tropane.

* * * * *